US007376557B2

(12) United States Patent
Specht et al.

(10) Patent No.: US 7,376,557 B2
(45) Date of Patent: May 20, 2008

(54) METHOD AND APPARATUS OF OVERLAPPING AND SUMMING SPEECH FOR AN OUTPUT THAT DISRUPTS SPEECH

(75) Inventors: Jeffrey Specht, Wyoming, MI (US); Daniel Mapes-Riordan, Evanston, IL (US); William DeKruif, Winnetka, IL (US)

(73) Assignee: Herman Miller, Inc., Zeeland, MI (US)

(*) Notice: Subject to any disclaimer, the term of this patent is extended or adjusted under 35 U.S.C. 154(b) by 65 days.

(21) Appl. No.: 11/326,269

(22) Filed: Jan. 4, 2006

(65) Prior Publication Data

US 2006/0247919 A1 Nov. 2, 2006

Related U.S. Application Data

(60) Provisional application No. 60/731,100, filed on Oct. 29, 2005, provisional application No. 60/684,141, filed on May 24, 2005, provisional application No. 60/642,865, filed on Jan. 10, 2005.

(51) Int. Cl.

| | |
|---|---|
| ***G10L 11/04*** | (2006.01) |
| ***G10L 21/00*** | (2006.01) |
| ***G10L 19/14*** | (2006.01) |
| ***G10L 17/00*** | (2006.01) |
| ***H03G 3/20*** | (2006.01) |
| ***A61F 11/06*** | (2006.01) |

(52) U.S. Cl. ...................... 704/225; 704/207; 704/208; 704/249; 381/57; 381/71.1

(58) Field of Classification Search ..................... None
See application file for complete search history.

(56) References Cited

U.S. PATENT DOCUMENTS

| | | | | |
|---|---|---|---|---|
| 3,541,258 A * | 11/1970 | Doyle et al. | ........... | 379/206.01 |
| 3,718,765 A | 2/1973 | Halaby | | |
| 3,879,578 A | 4/1975 | Wildi | | |
| 4,068,094 A | 1/1978 | Schmid et al. | | |
| 4,099,027 A | 7/1978 | Whitten | | |
| 4,195,202 A | 3/1980 | McCalmont | | |
| 4,232,194 A | 11/1980 | Adams | | |
| 4,438,526 A | 3/1984 | Thomalla | | |
| 4,852,170 A | 7/1989 | Bordeaux | | |
| 4,905,278 A | 2/1990 | Parker | | |
| 5,036,542 A * | 7/1991 | Kehoe et al. | ............. | 381/73.1 |

(Continued)

*Primary Examiner*—Richmond Dorvil
*Assistant Examiner*—Dorothy S Siedler
(74) *Attorney, Agent, or Firm*—Brinks Hofer Gilson & Lione

(57) ABSTRACT

A privacy apparatus adds a privacy sound based on a speaker's own voice into the environment, thereby confusing listeners as to which of the sounds is the real source. This permits disruption of the ability to understand the source speech of the user by eliminating segregation cues that the auditory system uses to interpret speech. The privacy apparatus minimizes segregation cues. The privacy apparatus is relatively quiet and thus easily acceptable in a typical open floor design office space. The privacy apparatus contains an A/D converter that converts the speech into a digital signal, a DSP that converts the digital signal into a privacy signal with pre-recorded speech fragments that are summed so that the speech fragments at least partly overlap one another, a D/A converter that converts the privacy signal into an output signal and one or more loudspeakers from which the output signal is emitted.

29 Claims, 19 Drawing Sheets

10

U.S. PATENT DOCUMENTS

| | | | |
|---|---|---|---|
| 5,355,430 A | 10/1994 | Huff | |
| 5,781,640 A | 7/1998 | Nicolino, Jr. | |
| 6,188,771 B1 | 2/2001 | Horrall | |
| 6,888,945 B2 | 5/2005 | Horrall | |
| 7,143,028 B2 * | 11/2006 | Hillis et al. | 704/203 |
| 2003/0091199 A1 | 5/2003 | Horrall et al. | |
| 2004/0019479 A1 | 1/2004 | Hillis et al. | |
| 2004/0125922 A1 * | 7/2004 | Specht | 379/88.01 |
| 2005/0065778 A1 | 3/2005 | Mastrianni et al. | |
| 2006/0009969 A1 | 1/2006 | L'Esperance et al. | |
| 2006/0109983 A1 | 5/2006 | Young et al. | |

* cited by examiner

20

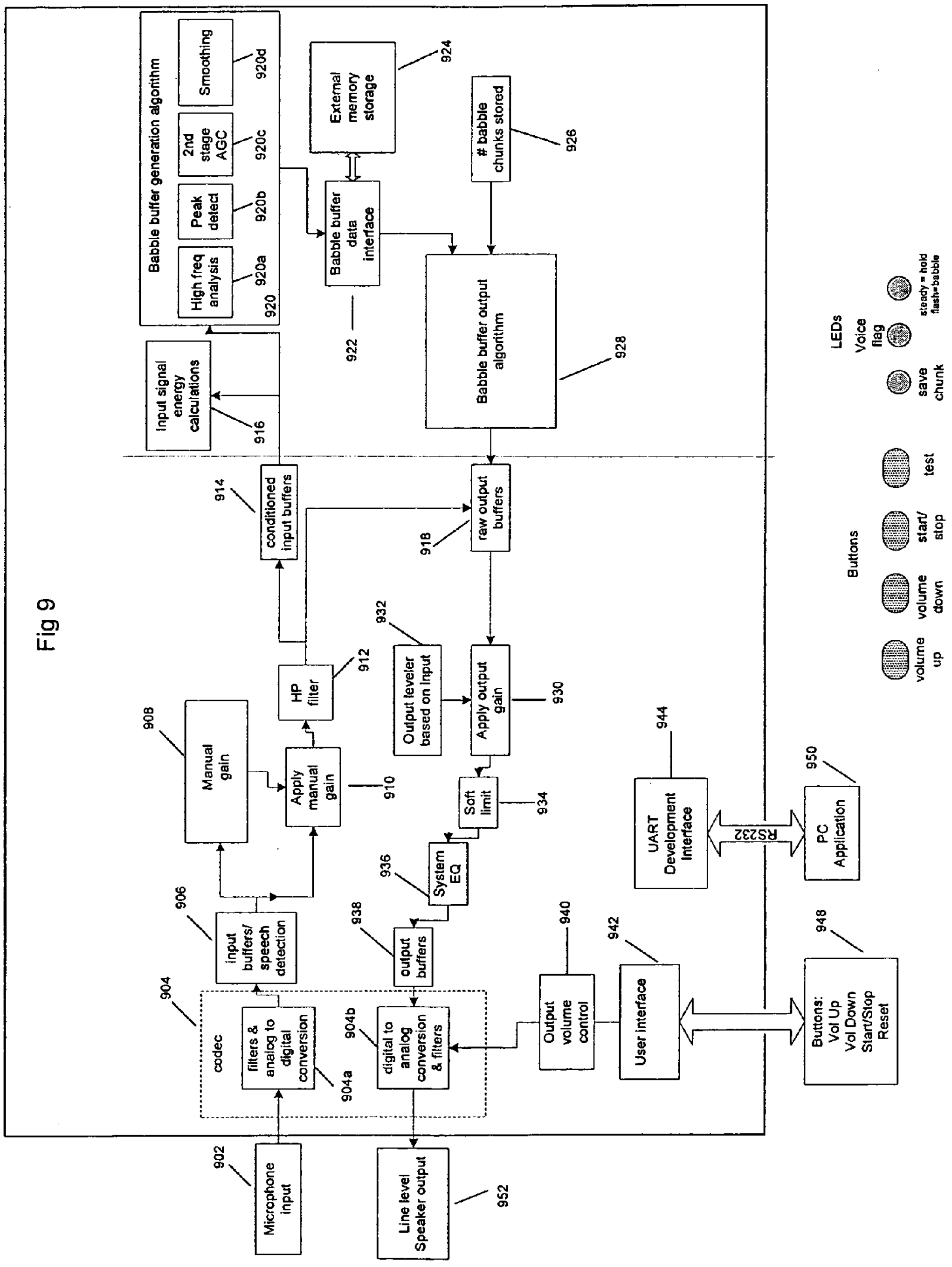
Fig 9
Microphone input
902
Line level Speaker output
952
codec
904
filters & analog to digital conversion
904a
digital to analog conversion & filters
904b
input buffers/ speech detection
906
Manual gain
908
Apply manual gain
910
HP filter
912
conditioned input buffers
914
Input signal energy calculations
916
raw output buffers
918
Babble buffer generation algorithm
920
High freq analysis
920a
Peak detect
920b
2nd stage AGC
920c
Smoothing
920d
Babble buffer data interface
922
External memory storage
924
# babble chunks stored
926
Babble buffer output algorithm
928
Apply output gain
930
Output leveler based on input
932
Soft limit
934
System EQ
936
output buffers
938
Output volume control
940
User interface
942
UART Development Interface
944
RS232
PC Application
950
Buttons: Vol Up Vol Down Start/Stop Reset
948
Buttons
volume up
volume down
start/ stop
test
LEDs
save chunk
Voice flag
steady = hold
flash=babble

METHOD AND APPARATUS OF OVERLAPPING AND SUMMING SPEECH FOR AN OUTPUT THAT DISRUPTS SPEECH

REFERENCE TO RELATED APPLICATIONS

This application claims the benefit of U.S. Provisional Application No. 60/642,865, filed Jan. 10, 2005, the benefit of U.S. Provisional Application No. 60/684,141, filed May 24, 2005, and the benefit of U.S. Provisional Application No. 60/731,100, filed Oct. 29, 2005. U.S. Provisional Application No. 60/642,865, U.S. Provisional Application No. 60/684,141, and U.S. Provisional Application No. 60/731, 100 are hereby incorporated by reference herein in their entirety.

FIELD

The present application relates to a method and apparatus for increasing privacy of a conversation and more specifically, a method and apparatus for increasing the privacy of a conversation using the speaker's own voice.

BACKGROUND

The acoustics of the environments that many people live and work in are often just accepted because there has not been the ability to affect much improvement. In the office environment particularly, acoustics remain a significant issue for many of the occupants. While the need for improved office sound management is clear, there are substantial needs beyond the confines of the office. An example are the recent changes in the law in Canada and the U.S. have placed strong new requirements on health providers to higher levels of confidentiality and privacy in their obtaining and handling patient information. The implementation of enhanced acoustic privacy is an evolving result of the implementation of these new laws. Health care facilities throughout the U.S. and Canada seek ways to provide the appropriate privacy for their patient interactions.

In a recent nationwide survey of corporate office workers commissioned by the American Society of Interior Designers, more than 70 percent of respondents indicated that their productivity would increase if their workplaces were less distracting. Always an issue, achieving acoustical privacy in open plan offices has become even harder in recent years. Contributing factors include the widespread use of speaker phones, the mixing of informal teaming or conference areas with personal cubicles, and the reduction of overall cubicle size, which has resulted in a significant increase in workstation density. In addition, new types of equipment, such as bigger computer monitors, provide a larger sound-reflective surface area within individual work spaces.

During the thirty years since the introduction of the open-plan workplace, manufacturers of office furniture have sought ways to improve the sound environment for open-plan office workers with only marginal success. All have recommended using a form of sound masking to augment the sound control provided by architecture elements (ceiling tiles and floor coverings) and the office furniture systems themselves.

Though often recommended, many users of the open-plan furniture do not implement any form of sound masking technology. The exact reasons vary by customer but in addition to high system and installation cost, there are issues with the complexity of the installation, intrusiveness of the sound masking system, and the lack of flexibility of such systems. Most sound masking systems are permanently installed in each location and do not easily adjust to changing office use plans. These systems are neither movable nor typically adjustable by the inhabitants (talkers). All those within the defined space of the sound masking system are exposed to its effects regardless of need or desire. In addition, the "white" or "pink" noise that is used in these masking systems is only marginally effective for enhancing speech privacy. White noise is a random noise that contains an equal amount of energy per frequency band. Pink noise has an equal amount of energy per octave. In order to create true speech privacy, white/pink noise systems, because of the technique they are based on, are set at a volume so high as to cause discomfort to those exposed to the systems. In summary, masking technology is substantially limited in its effectiveness and incapable of fulfilling the need for speech privacy in most applications within offices and other work spaces. In particular, speech privacy while using a telephone or other communication device is not addressed by current technology.

BRIEF SUMMARY

A privacy apparatus is provided that can be operated at lower amplitude than typical speech maskers while still affording the same or similar level of privacy. This privacy apparatus is based on generating an output stream that has speech fragments with certain characteristics that may be summed together so that the speech fragments at least partially overlap one another. One example of speech fragments with certain characteristics is speech fragments that exhibit characteristics of phonemes. The output stream is generated by summing phonemes so that the output stream has phonemes that overlap at least partly.

One way to generate the output stream with the summed speech fragments is by generating multiple voice streams using stored speech, summing the multiple voice steams, and outputting the summed multiple voice streams on loudspeakers positioned proximate to or near the talker's workspace and/or on headphones worn by potential listeners. The multiple voice streams may be composed of fragments of the talker's own voice, with the fragments being generating either during a training mode for the privacy apparatus or in real-time. A listener listening to sound emanating from the talker's workspace (which includes both the talker's speech and the multiple voice streams) may be able to determine that speech is emanating from the workspace, but unable to separate or segregate the sounds of the actual conversation and thus lose the ability to decipher what the talker is saying. In this manner, the privacy apparatus disrupts the ability of a listener to understand the source speech of the talker by eliminating the segregation cues that humans use to interpret human speech. In addition, since the privacy apparatus is constructed of human speech sounds, it is better accepted by people than white noise maskers as it sounds like the normal human speech found in all environments where people congregate. This translates into a sound that is much more acceptable to a wider audience than typical privacy sounds.

The privacy apparatus may receive voice input from the talker, and may process the voice input for use in generating the multiple voice streams. Processing the voice input may be performed during a training mode or in real-time (contemporaneously with generating the multiple voice streams). The processing may include analyzing the voice input to determine whether fragments of the voice input include certain types of speech, such as phonemes, "ss" sounds, plosives, etc. The types of speech may then be used to determine whether to store the speech fragments in a buffer (either for later use or for use in real-time) in generating the multiple voice streams.

Further, the privacy apparatus may produce the multiple voice streams from the talker's speech (such as the talker's voice fragments in the buffer) by a process of selecting at least some of the talker's speech signals (such as the talker's speech fragments) and assembling the selected speech signals into the voice streams. For example, for each of the voice streams, the talker's speech fragments may be randomly selected and assembled, so that the voice streams are uncorrelated with one another. As another example, the privacy apparatus may generate one voice stream, and then may insert a delay. The inserted delay may offset in time the voice stream, thereby generating other voice streams so that the voice streams are correlated with one another (e.g., generate a single voice stream of 1 minute in length, and offset the single voice stream by 15, 30 and 45 seconds to generate three additional voice streams).

Moreover, the privacy apparatus may generate the multiple voice streams in real-time or may store the multiple voice streams for replay later. If produced in real-time, the multiple voice streams may be combined for output onto separate channels of a loudspeaker. For example, eight separate voice streams may be generated, with four voice streams being combined for output on one channel of a stereo loudspeaker and the other four voice streams being combined for output on the second channel of the stereo loudspeaker. Fewer or greater number of voice streams may be combined for output, and fewer or greater number of channels may be used. If the multiple voice streams are stored for later use, the multiple voice streams may be stored in a variety of ways. For example, the multiple voice streams may be stored in an MP3 format (or other audio compression format) in a multi-channel format. Similar to the real-time output example, four voice streams may be combined and stored in one channel and another four voice streams may be combined in another channel. The combined voice streams may then be output, such as on a loudspeaker(s) and/or headphones.

Outputting the summed multiple voice streams may reduce the ability of the listener to discern the talker's speech. A listener, hearing the summed multiple voice streams, may be unable to discern the different voice streams. Rather, because the multiple voice streams are generated by the talker's voice, the listener may only be able to discern that the sounds are generated from the same talker. Further, because the multiple voice streams have certain characteristics, such as a random selection of phonemes, the listener exposed to the summed output may be less able to discern the talker's underlying speech. The summed multiple voice stream output exposes the listener to multiple types of sound simultaneously or near simultaneously. In the example of the multiple voice streams being generated by a random selection of phonemes, the listener may be exposed to 2, 3, 4 or more phoneme-type sounds simultaneously or near simultaneously since the phonemes may partially overlap one another. Exposing the listener to this multiple-type of sound may reduce the ability of the listener to discern the talker's underlying speech.

The privacy apparatus may be used in combination with another apparatus. For example, the privacy apparatus may be used in combination with a telephone, dictating machine, or the like. When a talker speaks into the microphone (or other voice sensor) of the telephone, the privacy apparatus may similarly receive the voice input and automatically generate multiple voice streams. The privacy apparatus may select the loudness at which the multiple voice streams are output based on the loudness of the talker's speech. For example, if the talker is speaking softly, the privacy apparatus may select a lower loudness level to output the multiple voice streams. Alternatively, the privacy apparatus may select a predetermined loudness regardless of the loudness of the talker's speech. The privacy apparatus may also be used as a standalone apparatus. For example, the privacy apparatus may be used to disrupt the conversation between two or more talkers. The multiple talkers may be identified in a variety of ways, and speech fragments for each of the identified talkers may be used in generating the multiple voice streams.

The foregoing summary has been provided only by way of introduction. Nothing in this section should be taken as a limitation on the following claims, which define the scope of the invention.

BRIEF DESCRIPTION OF THE DRAWINGS

FIG. 9 shows another example of a flow diagram for the input buffer storage and multiple voice stream generation from the stored input buffer.

DETAILED DESCRIPTION OF THE EMBODIMENTS

A privacy apparatus is provided that adds a privacy sound into the environment that closely matches the characteristics of the source (person speaking), thereby confusing listeners as to which of the sounds is the real source. The privacy apparatus may be based on a talker's own voice. This permits disruption of the ability to understand the source speech of the talker by eliminating segregation cues that humans use to interpret human speech. The privacy apparatus reduces or minimizes segregation cues. The privacy apparatus may be quieter than random-noise maskers and may be more easily accepted by people.

A sound can overcome a target sound by adding a sufficient amount of energy to the overall signal reaching the ear to block the target sound from effectively stimulating the ear. The sound can also overcome cues that permit the human auditory system segregate the sources of different sounds without necessarily being louder than the target sounds. A common phenomenon of the ability to segregate sounds is known as the "cocktail party effect." This effect refers to the ability of people to listen to other conversations in a room with many different people speaking. The means by which people are able to segregate different voices will be described later.

The privacy apparatus may be used as a standalone device, or may be used in combination with another device, such as a telephone. In this manner, the privacy apparatus may provide privacy for a talker while on the telephone. A sample of the talker's voice signal may be input via a microphone (such as the microphone used in the telephone handset or another microphone) and scrambled into an unintelligible audio stream for later use to generate multiple voice streams that are output over a set of loudspeakers. The loudspeakers may be located locally in a receptacle containing the physical privacy apparatus itself and/or remotely away from the receptacle. Alternatively, headphones may be worn by potential listeners. The headphones may output the multiple voice streams so that the listener may be less distracted by the sounds of the talker. The headphones also do not significantly raise the noise level of the workplace environment. In still another embodiment, loudspeakers and headphones may be used in combination.

Figure 1:
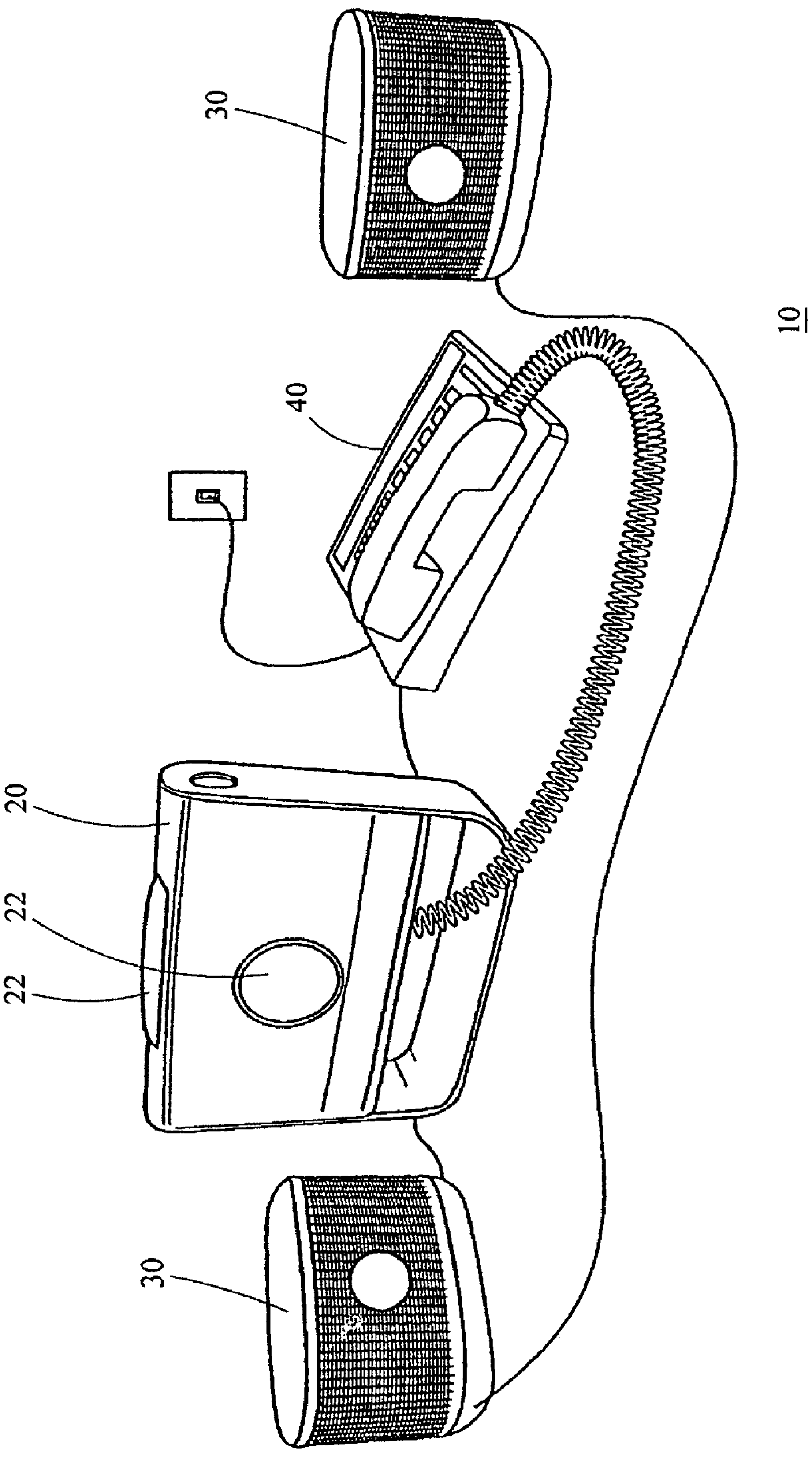
FIG. 1 is an illustration of a privacy apparatus in combination with a telephone.

FIG. 1 illustrates an overall view of the privacy apparatus 10 when used in combination with a telephone. The privacy apparatus 10 may contain a base unit 20 and loudspeakers 30. The base unit 20 may be rotatable on a bracket stand and may be connected to a telephone handset 40. The base unit 20 can be placed to the side or behind the telephone 40. The loudspeakers 30 may be connected to the base unit 20 and may be daisy-chained together. The loudspeakers 30 may be placed around the talker to provide a zone of speech privacy, such as at the top of panel walls (not shown). The base unit 20 may further contain a number of input devices, such as switches and a microphone, and output devices, such as light-emitting diodes (LEDs) 22. The loudspeakers 30 contain a volume control that may permit the talker to adjust the volume of each speaker individually. In the embodiment shown, the volume control is located under each speaker (and thus is not shown). Unlike conventional white noise maskers, the loudspeakers in the privacy apparatus 10 may all be pointed away from the talker.

More specifically, the bottom of the base unit 20 contains connection points and controls (not shown). The bottom of the base is accessed by rotating base unit 20 from bracket stand. In one embodiment, the base unit 20 contains four modular RJ11 style jacks. Two of the jacks are 4-conductor that are used to tap into the telephone handset microphone circuit by routing the handset to a jack and then another cable to where the handset cable normally attaches. The other two jacks are 6-conductor and are used to connect cables that run signal and power to the external speakers. A dipswitch block is used to properly configure the connection of the base (via the two handset jacks) to the various telephones that exist. A power connection jack may be used to allow the attachment of a UL approved wall mounted power adapter.

A side control panel may be covered when the base is sitting upright and in operation mode. The side control panel may be accessed when the base is rotated away from the bracket stand. The controls in the side control panel may include volume up and down buttons, gain setting and feature selection dip switches, and a 3 position mode selection slide switch (to select the training mode, gain adjustment mode, or operation mode). In a multi-user system, the 3 position selection switch may be used to select the training mode for user 1, the training mode for user 2, and the operation mode.

More specifically, the controls in the side control panel may include the mode selector, up and down switches, a speed adjustment dipswitch, a voice coverage adjustment dipswitch, and handset-headset selection/gain switches. The up and down switches may be momentary pushbutton switches (90 degree 100 gram force) for adjusting the loudspeaker volume in the operation mode and the gain in the training mode. The speed adjustment dipswitch may place the privacy apparatus into either a fast or slow (default) adjustment for the privacy sound output. The voice coverage adjustment dipswitch may place the privacy apparatus into either a full voice coverage or a limited (default) voice coverage mode in which the privacy apparatus only covers the talker's speech up to a preset volume level. The handset-headset selection/gain switches may allow the talker to configure the input device being used to control the volume of the privacy apparatus to set the gains correctly. The handset-headset selection/gain switches may be combined in a set of 6 and a set of 4 controls. The set of 6 may be located on the side and the set of 4 may be located on the bottom of the device.

An additional dip switch may be added that allows the talker to pick either a fast or slow ramp down of volume of the privacy sound after no speech is detected. Also, a dip switch may be added for talker to define if unit turns itself off after a defined period of no input or unit stays on but does not provide privacy sound after a defined period of no input. In the latter, the privacy apparatus may automatically restart.

In one embodiment of the privacy apparatus 10, stored speech may act as the source of privacy sound. Thus, after initial training, in which the privacy sound is stored in a non-volatile memory (not shown) in the base unit 20, the memory need not updated with further use. The built-in microphone on the privacy apparatus 10 may be used to collect good quality speech containing a sufficient frequency response to recreate near life-like speech sounds from the talker that is not possible with most telephone handset microphones. Once loaded into the non-volatile memory, the stored speech chunks may be kept until erased by the talker. The stored chunks may be used to generate the multiple voice streams. For example, the stored chunks may be randomly accessed to create the multiple voice streams, with the multiple voice streams being combined and output on two channels to create the privacy sound. In a multi-user system, the non-volatile memory may comprise store the speech chunks of the multiple users. For example, in a three person system, the memory may store the chunks of person 1 in a first memory location, the chunks of person 2 in a second memory location, and the chunks of person 3 in a third memory location, The connection to the microphone in the telephone 20 (or other input device) may be used to monitor the talker's voice level as he/she talks on the telephone 20. The privacy apparatus 10 may constantly match the output volume level of the privacy sound to the talker's voice level as they speak into the telephone 20. Or, the privacy apparatus 10 may output the privacy sound at a predetermined level regardless of the talker's voice level. An equalization filter (not shown) in the base unit 20 enables the privacy apparatus 10 to correct for frequency limitations in the privacy apparatus 10 by shaping the overall spectrum of the privacy sound for system compensation, such as microphone and loudspeaker responses, and to optimize the performance, system directivity, and sound quality.

The privacy apparatus 10 may have four modes: a power off mode in which the privacy apparatus 10 is not receiving power; a training mode in which the talker enters his/her voice into the memory to later create the privacy sound; a gain setting mode in which the gain of the privacy apparatus 10 is adjusted to match the input device's (e.g. handset or headset) output to the desired level of the privacy apparatus 10; and an operation mode in which the privacy apparatus 10 provides pre-recorded privacy sound (sound chunks or voice streams) when activated. In the operation mode, there are three sub-modes: a power on mode in which the privacy apparatus 10 has power but is not enabled; a privacy enabled mode in which the privacy apparatus 10 is turned on but is not picking up sound; and an active mode in which the privacy apparatus 10 is turned on, picking up sound and providing the privacy sound. These are described in more detail below.

Figure 2:
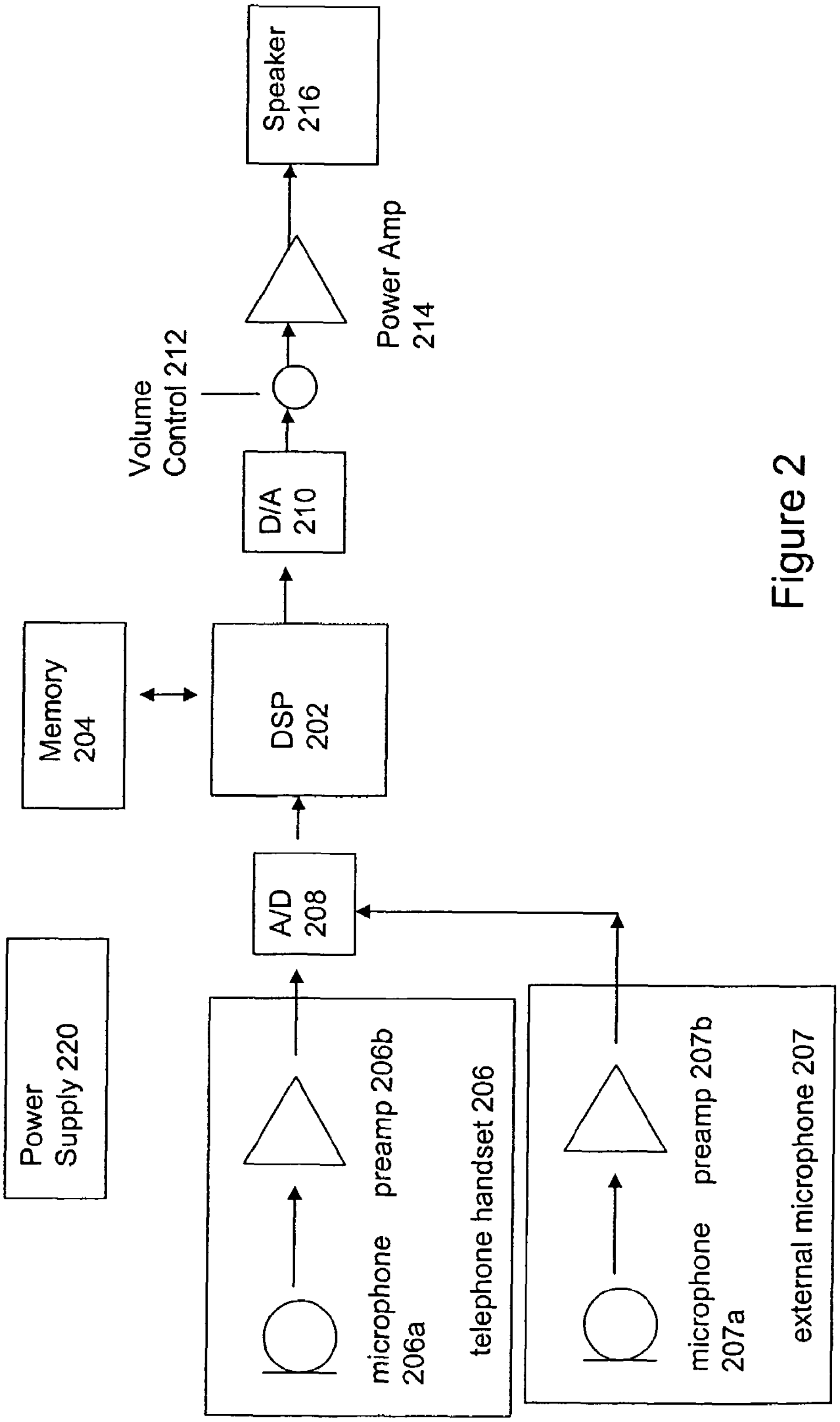
FIG. 2 is an example of a general block diagram of a privacy apparatus.

In more detail, FIG. 2 illustrates one embodiment of the privacy apparatus 200 used in combination with a telephone. The privacy apparatus 200 may include a digital signal processor (DSP) 202 which communicates with a memory 204. A telephone handset 206 contains a microphone 206*a*, into which a talker speaks, and preamplifier 206*b* that amplifies the signal from the microphone 206*a*. An external microphone system 207 may be used in the training mode and may contain an external microphone 207*a* into which a talker speaks, and preamplifier 207*b* that amplifies the signal from the external microphone 207*a*. The signal from the telephone handset 206 or external microphone system 207 may be supplied to an analog-to-digital (A/D) converter 208 that converts the analog audio stream into a digital signal. The digital signal may be fed to the DSP 202, processed by the DSP 202 to produce the desired privacy signal, and supplied to a digital-to-analog (D/A) converter 210 to convert the digital privacy signal back into an analog privacy signal. The volume of the analog privacy signal may be controlled using a volume control 212 such as a variable resistor and a power amplifier 214 before being supplied to one or more loudspeakers 216. Power to various circuitry may be supplied by a power supply 220.

Figure 3:
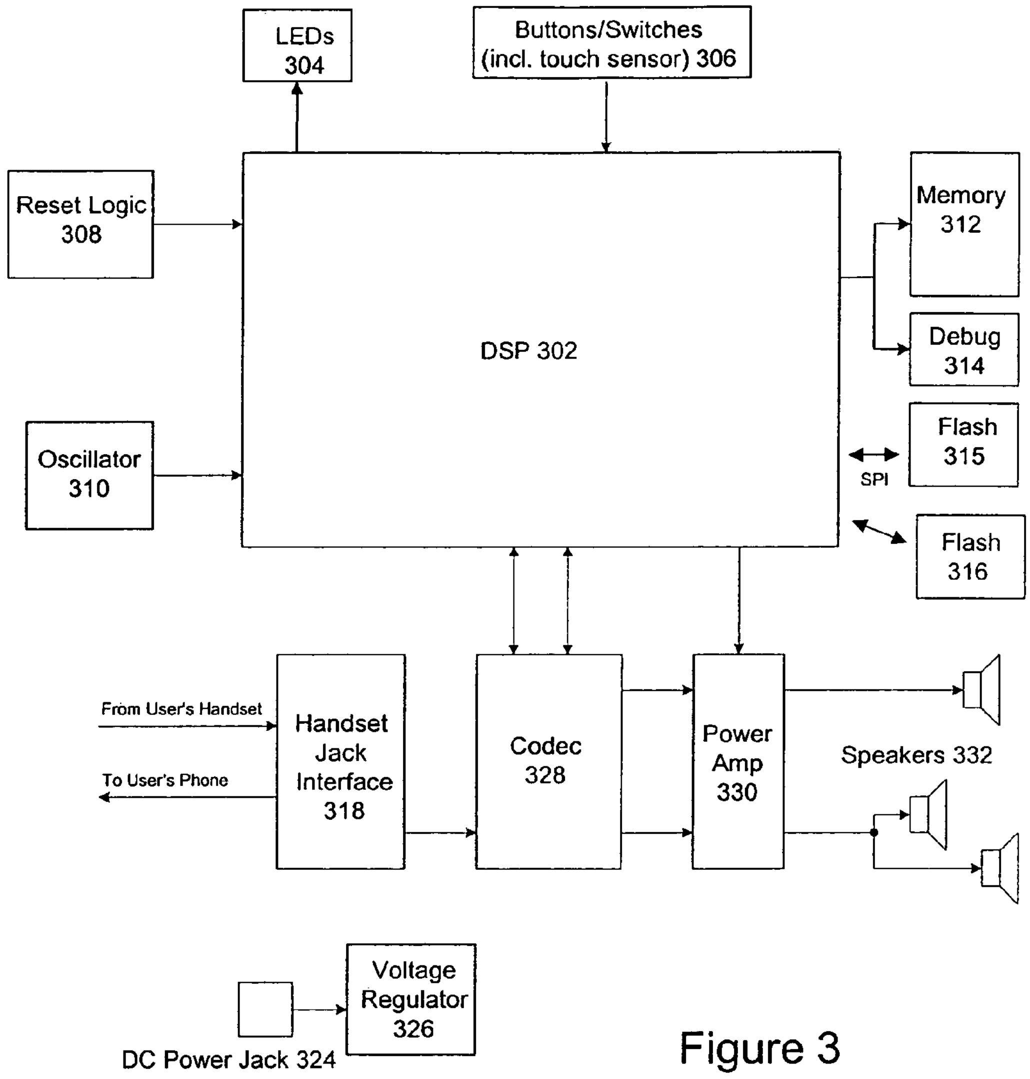
FIG. 3 is a block diagram of a base unit of the privacy apparatus depicted in FIG. 1.

FIG. 3 shows an example of an expanded block diagram of the base unit 20 of the privacy apparatus. As shown in FIG. 3, the privacy apparatus may include a base unit 20. The base unit 20 may be disposed on a printed circuit board (or PCB, which is not shown). The base unit 20 may contain the DSP 302. The DSP 302 can be any known DSP, for example, a 55x series DSP such as a TMS 320VC 5507 Series or similar DSP with 128 KB of internal RAM, or a TMS 320VC 5509 Series or similar DSP with 256 KB of RAM.

The DSP 302 may receive signals from various internal and external inputs. The external inputs may include buttons and/or switches 306. These buttons and/or switches 306 may include one or more volume up/down buttons, a power on/off button, a reset button, one or more headset receive volume buttons, a main power switch and/or handset selection switches, which will be described in more detail below. The internal inputs include logic that enables a reset of the components in the DSP (reset logic 308), a local oscillator 310, and a flash memory 316. The DSP 302 may provide signals to various internal and external outputs. The external outputs may include display devices such as LEDs 304. The LEDs 304 or other displays indicate, for example, that power to the base unit 20 is on, that a microphone signal is detected, that a microphone input is underdriven or overdriven (used in a training mode), and that the output is active. The internal outputs may include a memory 312 and debug base 314 which permits debugging of the DSP 302, if necessary.

In one embodiment, multiple flash memories 315, 316 are provided. A firmware download feature may or may not be included, as desired. The flash memory 316 may be programmed prior to being placed on the PCB. The PCBs may be fitted with a dual footprint, which accepts a plastic leadless chip carrier (PLCC) socket so various chips may be easily removed for reprogramming. The flash memory 316 may store the DSP code and a block may be set aside to store configuration parameters, such as the volume control setting and the handset gain settings for the handset being used.

The flash memory 315 may store audio chunks or other speech input. The functions of flash memory 315, 316 are separated so that the program memory is not written to during use, thereby avoiding the risk of corrupting the DSP code if the setting updates are written and the audio stream stored on one flash. However, if desired, a larger flash memory of, say, 16 Mb can be used for both purposes.

The use of flash memory 315 permits permanent, non-volatile storage of the audio stream as well as controls for the DSP and permits the external memory 312 to be eliminated. Alternatively, a memory such as a 4M×16 SDRAM can be used to provide storage of audio stream in lieu of the flash memory 316. A table of a typical memory storage vs. audio buffer length for such memory (assuming, for example, 16-bit samples) is shown in Table 1, below:

TABLE 1

Sample rate vs. Buffer Time

| Sampling Rate | Max Audio Frequency | Buffer time (seconds) |
|---|---|---|
| 32 ksps (kilosamples/sec) | 16 kHz | 125 |
| 24 ksps | 12 kHz | 167 |
| 16 ksps | 8 kHz | 250 |
| 12 ksps | 6 kHz | 333 |

The A/D and D/A conversion mentioned above may be handled in a Codec 328. The Codec can be implemented in software, hardware (such as integrated circuits or chips), or a combination of both. The Codec 328 receives signals from the handset through a handset jack interface 318 as well as the DSP 302. The Codec 328 may transmit signals to the DSP 302, a power amplifier 330, and loudspeakers through remote person speaking jacks 334.

Figure 4:
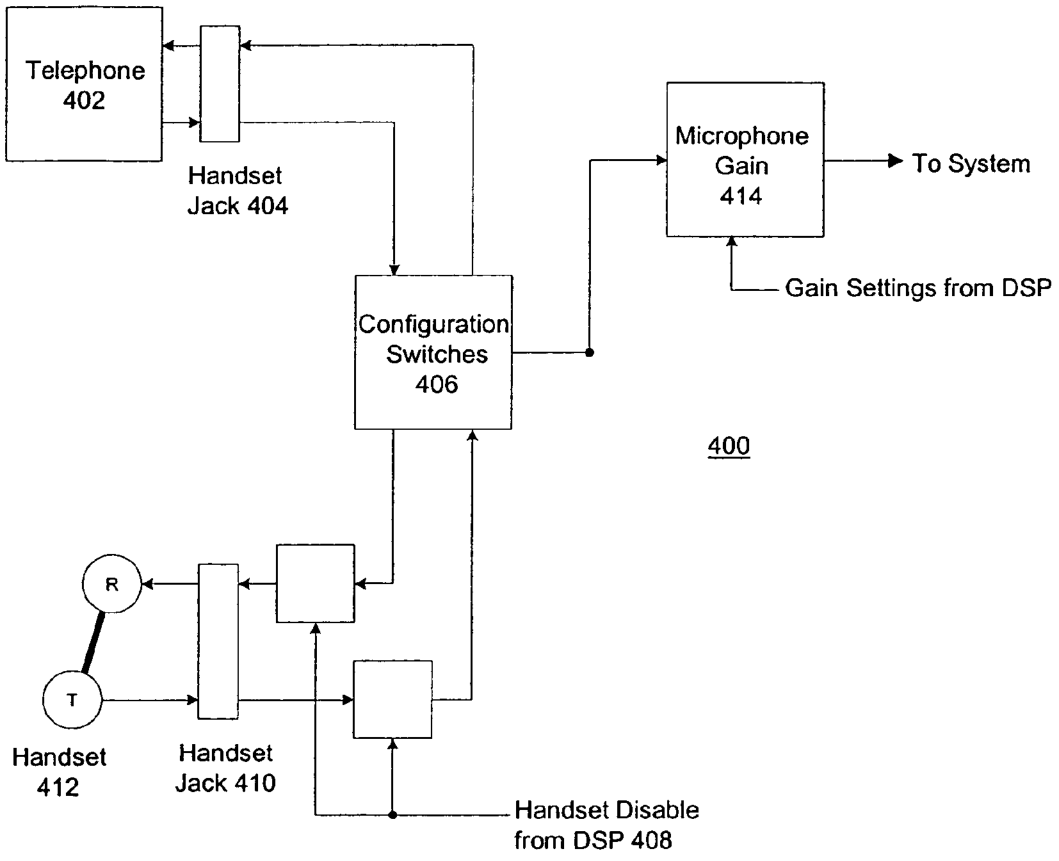
FIG. 4 is an example of a block diagram of handset and headset interfaces of the privacy apparatus.

Referring to FIG. 4, there is shown an example of a block diagram of handset and headset interfaces of the privacy apparatus. Any known Codec may be used as the Codec depicted in FIG. 4. One viable Codec is a 2-channel TI AIC23 Codec. With a 12.288 MHz crystal frequency, this Codec will support sampling rates of 48, 32, 24, 16, and 8 ksps The Codec may also has an internal anti-alias filter which provides >60 dB of rejection at audio frequencies above 0.584 times the sampling rate. For example, at 32 ksps, the anti-alias filter response is −60 dB at 18.7 kHz. Only a single channel is used for input A/D conversion. The maximum input level to the Codec is nominally 1 Vrms, although the Codec input gain can be adjusted over a −34.5 to 12 dB range. Both channels are used for D/A conversion of audio streams. The maximum output level is 1 Vrms. If a headphone output of the Codec is used, the gain can be adjusted to over the −73 to 6 dB range. The Codec headphone outputs may be used to drive all loudspeakers. The loudspeakers may have built-in volume controls, the volume control on the base unit 20 can adjust all loudspeakers equally, and the control on the loudspeaker may then be used to adjust the balance between the loudspeakers. The loudspeakers may include only external loudspeakers, which are remote from the enclosure covering the DSP, memory, etc. or may also include loudspeakers internal to the base unit 20.

The base unit 20 may also include a power amplifier 330 that supplies a signal to the loudspeakers 332 and jacks to external equipment such as to an optional headset, DC power, and/or the loudspeakers. The DC power jack 324 may be a coaxial power connector that provides power for a voltage regulator 326 that supplies regulated 5V DC power to the base unit 20. Any UL-certified power adapter can be used as the voltage regulator 326. The voltage regulator may be sized to accommodate driving multiple loudspeakers.

In one embodiment, a 2-channel power amplifier 330 may be used to drive the loudspeakers 332. This permits a sound pressure level (SPL) of at least 80 dB at 1 meter to be attained when using the loudspeakers 332. It may be desirable that the background noise floor of the loudspeakers (at 1 m) is well below the typical quiet office ambient noise level of 40 dBA. The base may be fitted, as shown in FIG. 1, with two identical loudspeakers that are daisy-chained or, as shown in FIG. 3, with three identical loudspeakers. In the latter case, two of the loudspeakers may be fed as a pair, and the remaining loudspeaker may be fed independently from the power amplifier output channels. One desired frequency response, based on the measured JBL Duet loudspeakers is +/−3 dB over 150-7 kHz. A JBL Duet loudspeaker exhibited a measured sensitivity of 82 dB/W SPL at 1 m on axis at 1 kHz, which represents one goal in selecting suitable loudspeaker drivers. In one embodiment, the output is limited to a maximum average sound pressure level (SPL) of about 70 dBA SPL.

The loudspeakers may incorporate internal power amplifiers and are fed with a line level (nominal max 1 V rms) signal from the base 100. DC power can be fed to the loudspeakers from the base unit 20 over the same multi-conductor cable with the line level audio. A non-standard jack (i.e. one not used for PC loudspeakers) may be selected which provides a ground connection as well as signal leads for both audio channels. Additionally, a conductor may be provided for DC power feed to the loudspeakers. A separate volume control or switching for the loudspeakers may be used if desired.

The headset jack, if present, may communicate with the remaining portions of the base unit 20 through a headset interface. In one embodiment, talkers can connect up stand-alone headset by connecting their headset between the telephone handset and the base. The base unit may then connect to the telephone as normal. The talker then has the option to set up the unit to operate with either their telephone handset or the headset system. A handset communicates with the base through a handset jack interface 318.

Referring to FIG. 4, there is shown an example of a block diagram of general hardware/software in a DSP of the privacy apparatus including details of the handset interface. Handset jacks 404 and 410 separately may provide communication between the telephone 402 and the handset 412. As shown, both the input and output communication paths between the handset jack 410 for the handset 412 and configuration switches 406 may be disabled by a signal from the DSP. The configuration switches 406 control not only the handset 412 and telephone 402, but in addition various aspects of the microphone and headset, if present. For example, as shown, the configuration switches 406 along with the DSP control the gain of the microphone 414.

In an embodiment in which a headset is used, the configuration switches may be used to control the headset transmitter gain and headset receiver gain. In this case, the controls may be transmitted to and feedback is received from the headset through a headset jack. The DSP may also receive signals from the headset through the headset jack.

More specifically, the handset jack interface circuitry 400 may have several functions. The handset jack interface circuitry may pick off the audio transmitted from the handset connector 410 of the talker's telephone handset 412 using a transformer-coupled amplifier. The transformer may also provide high voltage isolation. In addition, since the population of handsets use different wires on the 4-conductor handset cable for a transmit audio path, the handset jack interface may allow the talker to select which two wires are used for the audio pick-off. The handset jack interface circuitry may also allow for gain adjustment since the population of handsets has a gain variation of 60 dB. The handset jack interface circuitry additionally may pick off and transformer isolates the audio received from the telephone 402, which may be subsequently sent to an optional headset.

The ability to select the correct wires for the transmit and receive pick off are implemented by configuration switches 406 such as a multi-pole DIP switch. This switch pole may be dedicated to a coarse gain adjustment, while an additional pole places the base in a training mode. The volume up/down buttons have multiple functions. The volume up/down buttons switch functionality and adjust the base transmit pick-off gain, that is, depending on the function set by a slide or another switch, the buttons control the input gain of the signal from the external microphone system in the training mode, or control the input gain of the signal from the handset microphone or the output volume of the signal sent to the loudspeakers in the operation mode. For example, when the volume up/down buttons are set to control the input gain of the handset microphone, the DSP counts the number of actuations from the up/down buttons and provides a 3-bit binary output, which controls an attenuator in the handset interface circuit. The sensitivity setting is stored in the non-volatile memory.

As noted above, although a handset is generally used, in an alternative embodiment, the base unit 20 may accept a commercially available headset, chosen by the talker from a group of pre-approved headsets. The headsets may be selected to provide extended frequency response (to 7 kHz). As is the case with the handset interface, adjustment of the gain and wiring configuration is provided that is appropriate to the particular make and model of telephone used. The talker is able to set his/her receive audio level in the headset through adjustable gain stages, which are implemented under control of the DSP. Dedicated headset volume up/down buttons on the base may be used to control the headset.

Turning now to the ability of the auditory system to determine individual sounds from a number of overlapping sounds, the auditory system exploits segregation cues to separate, for instance, different voices in a crowd. These cues refer to differences between sound sources in: spatial localization, onset and offset time, loudness, harmonic structure, and spectral shape (timbre), as well as visual cues. The sound created minimizes these cues, thereby making the real source ambiguous. Using energy sufficient to overcome the target signal, as described above, may further improve the effects of cue minimization.

The human auditory system may use the differences in timing and level between the input at each ear to perform spatial localization. By appropriate placement of loudspeakers of the privacy apparatus, the minimization of localization cues may be controlled. The placement may depend on whether there is a direct line of sight between the talker and listener (direct field) or whether there is a barrier (e.g., cubicle wall) between them (indirect field). For direct field applications, placing a loudspeaker on the line between the talker and listener may reduce or minimize localization cues. The ability of listeners to localize sources in the indirect field is much worse than in the direct field. Although it depends on the acoustics of the space, in one example, the loudspeaker can be as much as 90 degrees or more off the direct line axis when there is a barrier between the talker and listener.

The auditory system can also segregate sources if the sources turn on or off at different times. The privacy apparatus may reduce or minimize this cue by outputting a stream whereby random speech elements are summed on one another so that the random speech elements at least partially overlap. One example of the output stream may include generating multiple, random streams of speech elements and then summing the streams so that it is difficult for a listener to distinguish individual onsets of the real source. The multiple random streams may be summed so that multiple speech fragments with certain characteristics, such as 2, 3 or 4 speech fragments that exhibit phoneme characteristics, may be heard simultaneously by the listener. In this manner, when multiple streams are generated from the talker's voice, the listener may not be able to discern that there are multiple streams being generated. Rather, because the listener is exposed to the multiple streams (and in turn the multiple phonemes or speech fragments with other characteristics), the listener may be less likely to discern the underlying speech of the talker. Alternatively, the output stream may be generated by first selecting the speech elements, such as random phonemes, and then summing the random phonemes.

The auditory system is also known to exploit level differences between sources in order to segregate them. The privacy apparatus may control level cues and may be operated at a level that may be about 4-10 dB, for example, 9 dB, above the source level as measured at the listener. Above 9 dB, a loudness cue can be exploited if it is accompanied by another segregation cue (e.g., spatial difference). Loud sounds may also produce more privacy by reducing the ability of the hair cells in the inner ear to respond to the weaker signal. Although a loudness segregation cue has been shown with small (3-6 dB) level differences, the effect is minor and can be considered a secondary effect. The level may also be limited for other reasons.

Harmonic structure cues refer to the differences in the fundamental pitch and associated harmonics between the source and privacy apparatus. The auditory system may use the harmonic structure of speech sounds as one of the features to reconstruct the intended words spoken by the talker. The privacy apparatus reduces or minimizes this cue by using the talker's own speech as a basis for creating the privacy sound. Although the short-term pitch and harmonics differ between the source and the privacy apparatus, the spectral range of the pitch and harmonics of the privacy sound may overlap the source's range. This constant overlap may confuse the auditory system as it attempts to reconstruct the words spoken by the source. The privacy apparatus accordingly reduces or minimizes system distortion as this distortion provides a means of segregation due to the differences between the original sounds and the distorted sounds.

Spectral shape cues refer to differences in the total average spectrum (both harmonic and inharmonic content) between the source and privacy apparatus. Such differences are often referred to as timbre cues. The privacy apparatus minimizes this cue by using samples of the source sound as the privacy sound, thus the privacy sound has the same timbre. In addition, the frequency response of the privacy apparatus is relatively flat so as not to impart a spectral shape difference in the privacy apparatus. One parameter regarding spectral shape segregation cues is the high frequency limit of the privacy apparatus. Experiments have shown that a high frequency limit of 3 kHz is inadequate to produce privacy. Increasing this limit to 7 kHz produces a substantial increase in privacy performance. Further increasing this limit to 14 kHz may produce very little improvement in privacy performance, depending on the source characteristics of the talker.

However, the microphones found in most conventional telephone handsets and headsets only extend to about 3 kHz. This means that, as the frequency limit used to create the privacy sound extends to at least about 7 kHz, the microphones in typical handsets are not used to create the speech fragments which eventually are used to create the privacy sound. Instead, a dedicated microphone (shown in FIG. 2 as microphone 207*a*) with the desired frequency response is disposed on the PCB in the privacy apparatus. This microphone may be activated with one of the external inputs when the privacy apparatus is in setup/training mode and either active or inactive when in the normal privacy mode. The microphones in typical handsets are used to adjust the output volume of the privacy apparatus in the operation mode. Of course, if a particular handset contains a microphone with a frequency response of up to about 7 kHz or greater, the separate microphone may be eliminated.

Visual cues also remain a means by which the human auditory system segregates sounds. If the listener can see the talker, the listener may be able to read the lips of the talker to reconstruct the source words. In this manner, the microphone may be constructed to conceal a part or all of the lips of the talker. For example, the microphone of the talker may comprise a headset. The headset may be used in combination with a telephone, dictating machine or the like. The headset may be formed such that a part or all of the lips or mouth region of the talker may be concealed. For example, the headset may include an additional piece, such as a plastic attachment, that may abut the microphone of the headset. The shape of the additional piece may be oval or circular. In this manner, the additional piece may reduce the visual cues and may partly muffle the sound of the talker.

Figure 5:
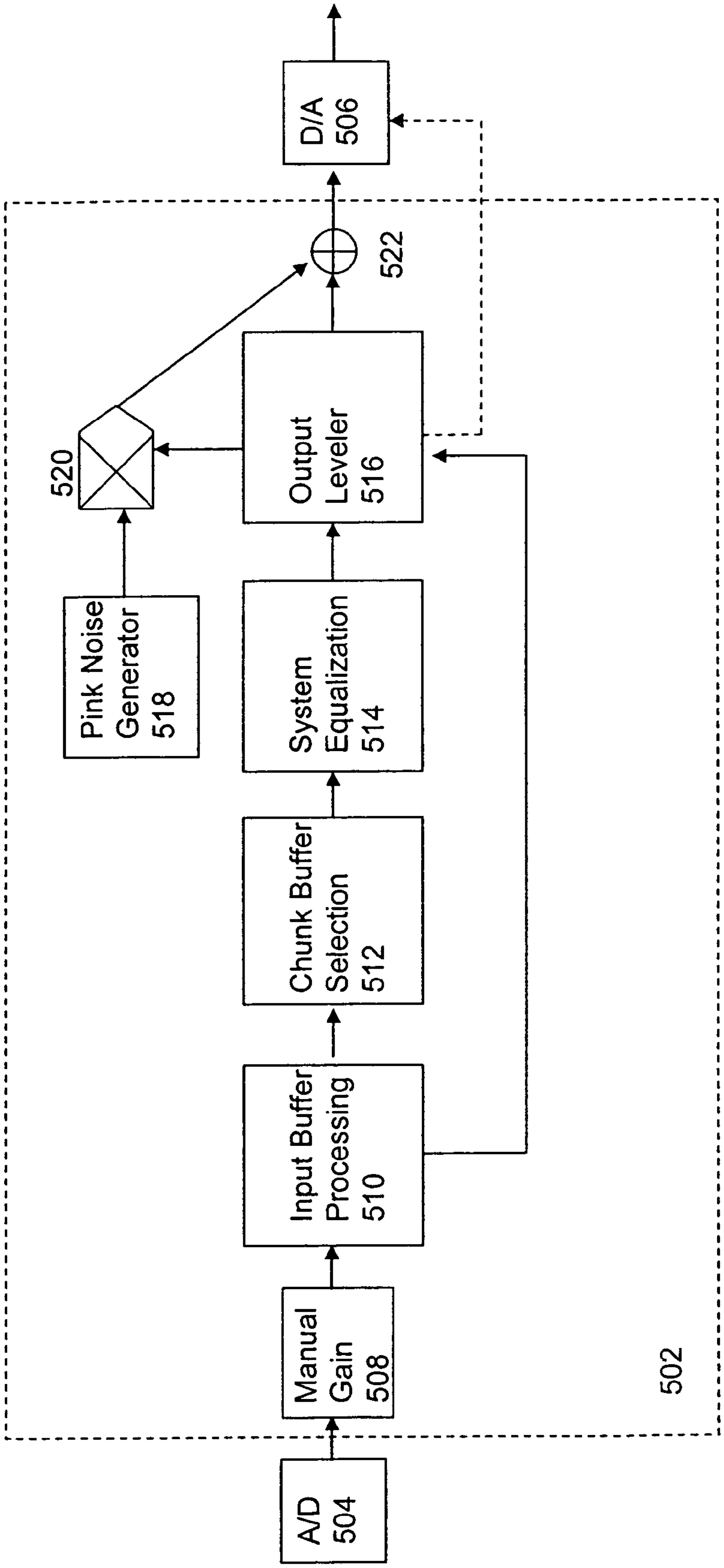
FIG. 5 is an example of a block diagram of general hardware/software in a DSP of the privacy apparatus.

Now, specifics of the DSP and privacy apparatus will be further discussed. FIG. 5 illustrates a diagram of the software blocks in the DSP. As indicated previously, the privacy apparatus 500 includes the DSP 502, the A/D converter 504 that converts the target sound into a digital signal for the DSP 502 to process, and the D/A converter 506 that receives the processed signal from the DSP 502 to supply to the loudspeakers to create the privacy sound. The A/D converter 504 and D/A converter 506 may be contained within the Codec.

The DSP 502 may contain a manual gain 508 to which the digital signal from the A/D converter 504 may be supplied. The manual gain 508 may increase the signal level from the microphone. The manual gain 508 may provide an overall gain change range of approximately +/−15 dB. The A/D converter 504 may also change the analog gain prior to digitization, which is useful for optimizing the overall system signal-to-noise ratio (SNR).

An automatic gain stage (AGC) (not shown) may adjust the overall average power in each gated input (called an input chunk) to a predetermined target level. Chunks are alternatively referred to as speech fragments. The AGC may correct for inaccuracies of the manual gain 508 due to the slow time constant used in adjusting the input gain. The AGC may measure the power in the input chunk, compare the power to the target average gain level, and apply a gain factor to each sample in the input chunk so that the power of the input chunk matches the power of the target level.

The privacy signal from the manual gain 508 may be provided to an input buffer processor 510 and may then be selected by a chunk buffer selection, which selects the chunk of voice or voices to play, equalized by a system equalizer 514, and the output of the equalizer 514 is leveled/limited by an output leveler 516.

The input buffer processor 510 may contain a speech detection block to distinguish the beginning/endings of speech. The output leveler may use the speech detection block to gate its operation. The speech detection block detects the presence of a voice signal that has a detection algorithm includes a speech signal level with a relatively fast time constant (~10 ms) and a background noise level estimator with a relatively slow time constant (~2 s). The signals from the input buffer processor 510 may change when the speech level estimator rises above a noise floor estimator by a preset factor. The signal feeding the speech level estimator is bandpass filtered to emphasize typical speech frequencies. Additional processes may also be used to detect speech input so as to minimize signal changes due to non-speech sounds. For example, a zero-crossing detector may be used to differentiate periodic vowel sounds from other sounds. In addition, a minimum onset time can be established so that sudden loud noises (e.g., a door slam) do not trigger speech detection.

In another embodiment, pink (or white) noise from a pink (white) noise generator 518 may be added to the signal from the output leveler 516 by an adder 522 and then supplied to the D/A converter 506. In this case, the level of pink noise from the pink noise generator 518 supplied to the adder 522 may be adjusted using a gain stage 520 controlled by the signal from the output leveler 516. This embodiment depicts the generator and associated circuitry; although, the generator and associated circuitry may be removed if desired.

In another embodiment, the DSP may contain a gated AGC to which the digital signal from the A/D converter is supplied rather than a manual gain. The AGC may increase the signal level from the microphone. The AGC may be triggered ("gated-on") by the presence of a voice signal and frozen ("gated-off") when no voice signal is present. The AGC may use the speech detection mechanism for the gating. The AGC may operate in a feed forward manner and provide an overall gain change range of approximately +/−15 dB.

The privacy apparatus may be operated in a variety of ways. In one way, shown in FIGS. 6A-D, the privacy apparatus operates in a set of modes, including a voice input mode (for generating the speech fragments), input gain adjust mode (for adjusting the gain for the output of the voice streams), and use mode (for generating the plurality of voice streams in order to disrupt the speech of a talker or multiple talkers. In another way, the privacy apparatus may operate such that the voice input mode and use mode operate concurrently (e.g., the speech fragments are generated contemporaneously with generating the plurality of voice streams).

FIGS. 6A, 6B, 6C and 6D are flowcharts showing operation of the privacy apparatus in separate modes. Before operation, the privacy apparatus may be installed in a workspace, or other office or home environment. To install the privacy apparatus, the base of the privacy apparatus may be placed, for example, on a desktop behind or next to a telephone. The AC adapter of the privacy apparatus may then be plugged into an available power source. The base may be connected to the telephone using a phone-in connector and a handset-out connector. The loudspeakers may be positioned in areas in which the talker wishes to have privacy and the loudspeakers may then be connected to the base unit with left and right speaker connectors. The talker may then choose the telephone and gain settings, confirm the slow speed for the output and the default voice volume limit adjustment.

Figure 6A:
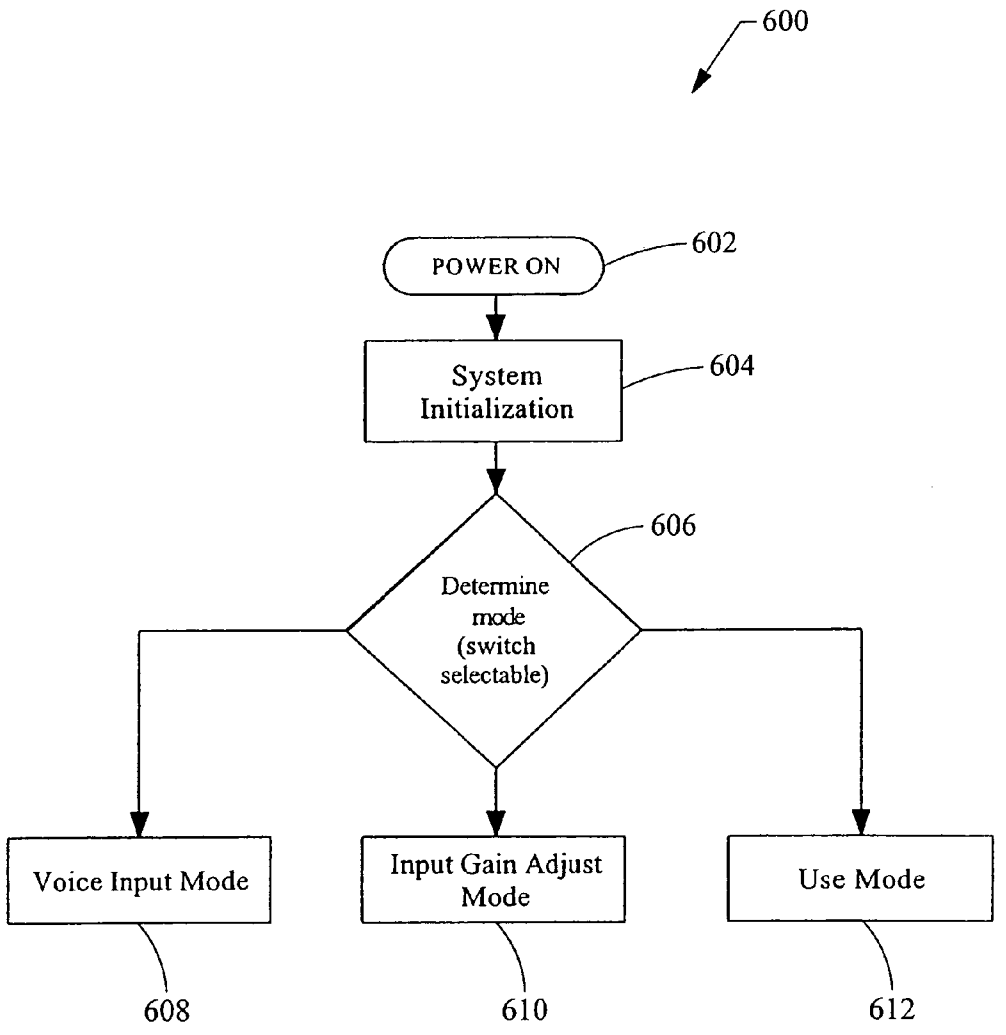
FIGS. 6A, 6B, 6C, and 6D are examples of flow charts of processes in the privacy apparatus during operation in different modes.

When the privacy apparatus is first turned on, as shown in block 602 of FIG. 6A, the privacy apparatus may initialize, as shown at block 604. After initialization, the privacy apparatus may determine which mode has been selected for the privacy apparatus using the 3 way switch, as shown at block 606. If the training (voice input) mode has been selected (block 608), the privacy apparatus may enter the training mode (see FIG. 6B). If the input gain adjust mode has been selected (block 610), the privacy apparatus may enter the input gain adjust mode (see FIG. 6C). If the operation (use) mode has been selected (block 612), the privacy apparatus may enter the use mode (see FIG. 6D).

Figure 6B:
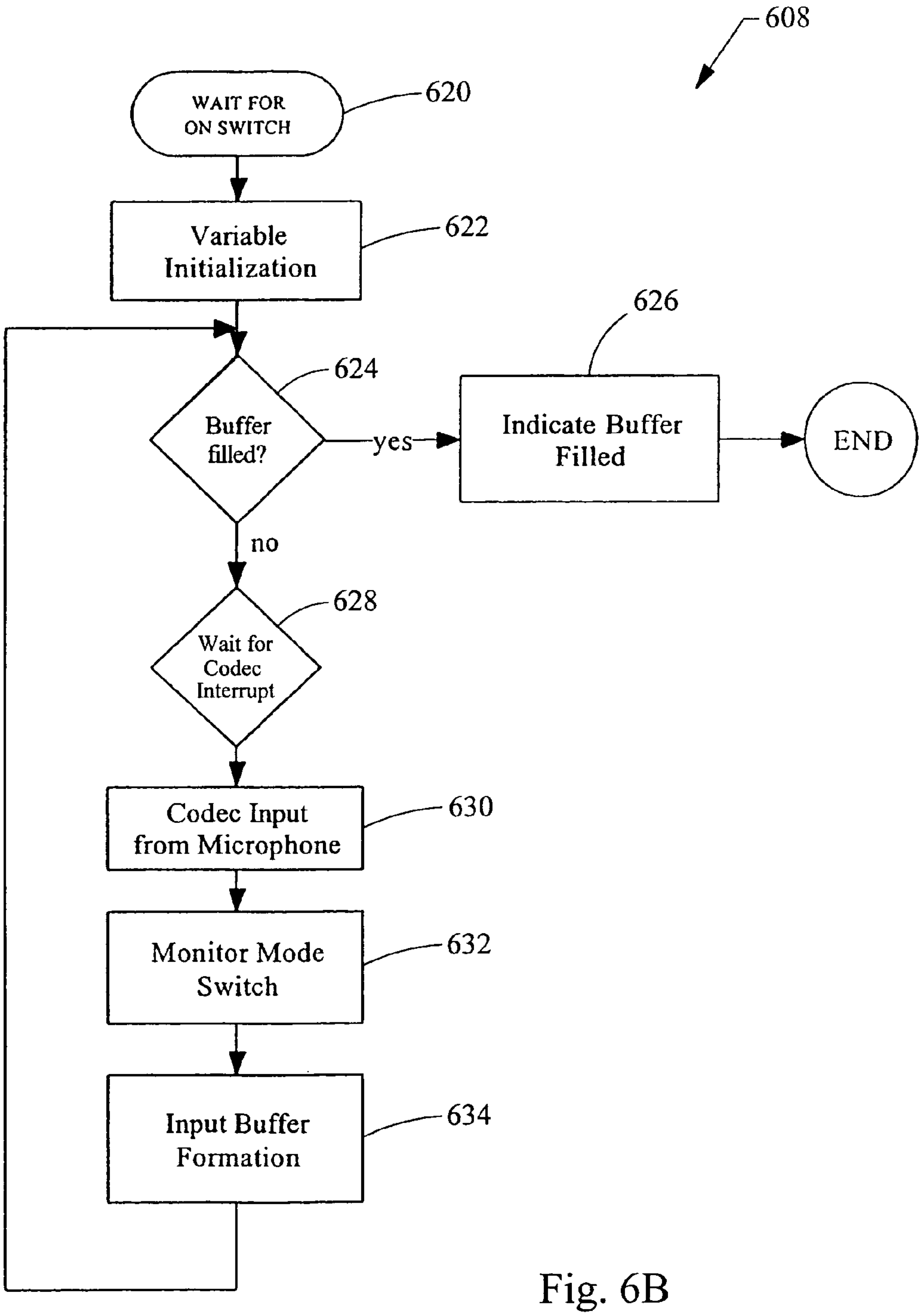

To select the training mode, as shown in the flow diagram 608 in FIG. 6B, the talker may swing the base so that it is positioned on its side with a light pipe, fed by an amber microphone LED surrounding the microphone, positioned towards the talker. The microphone may be approximately centered with the talker's head. The talker may choose to either disconnect all the cables (except power) or not. The talker may place the privacy apparatus into training mode using the mode selector switch (block 620) and turn on the privacy apparatus. As shown at block 622, the variables in the privacy apparatus may initialize once the privacy apparatus is turned on and the training mode is selected. The amber LED is lit and blinking when in the training mode.

The privacy apparatus may determine whether the buffer memory is filled, as shown at block 624. If it is, the amber LED may indicate this to the talker (block 626) and/or an audible sound may be generated, and the privacy apparatus may be used immediately if the buffer memory contains input from the talker. If the buffer memory is not filled, the system waits for the codec interrupt, as shown at block 628. In this case, the talker may test his/her voice volume by reading a test sentence into the microphone and watching the privacy apparatus for feedback regarding his/her voice levels.

A top oval touch switch provided as a touch sensor (capacitance sensor) located on the top of the base is surrounded by another light pipe. This light pipe is connected to blue and amber LEDs and has three sections: an upper amber section, a lower amber section, and a middle blue section. The light pipe provides different feedback to the talker depending on the mode. The oval control on the top of the base highlights to show the talker that his/her voice is being input correctly. When the light is blue and centrally located, the talker is within the correct range. When the light is amber, and either below or above the center point, the talker may adjust his/her voice. If the upper amber section turns on, the talker is speaking too loudly, and if the lower amber section turns on, the talker is speaking too softly.

Figure 7A:
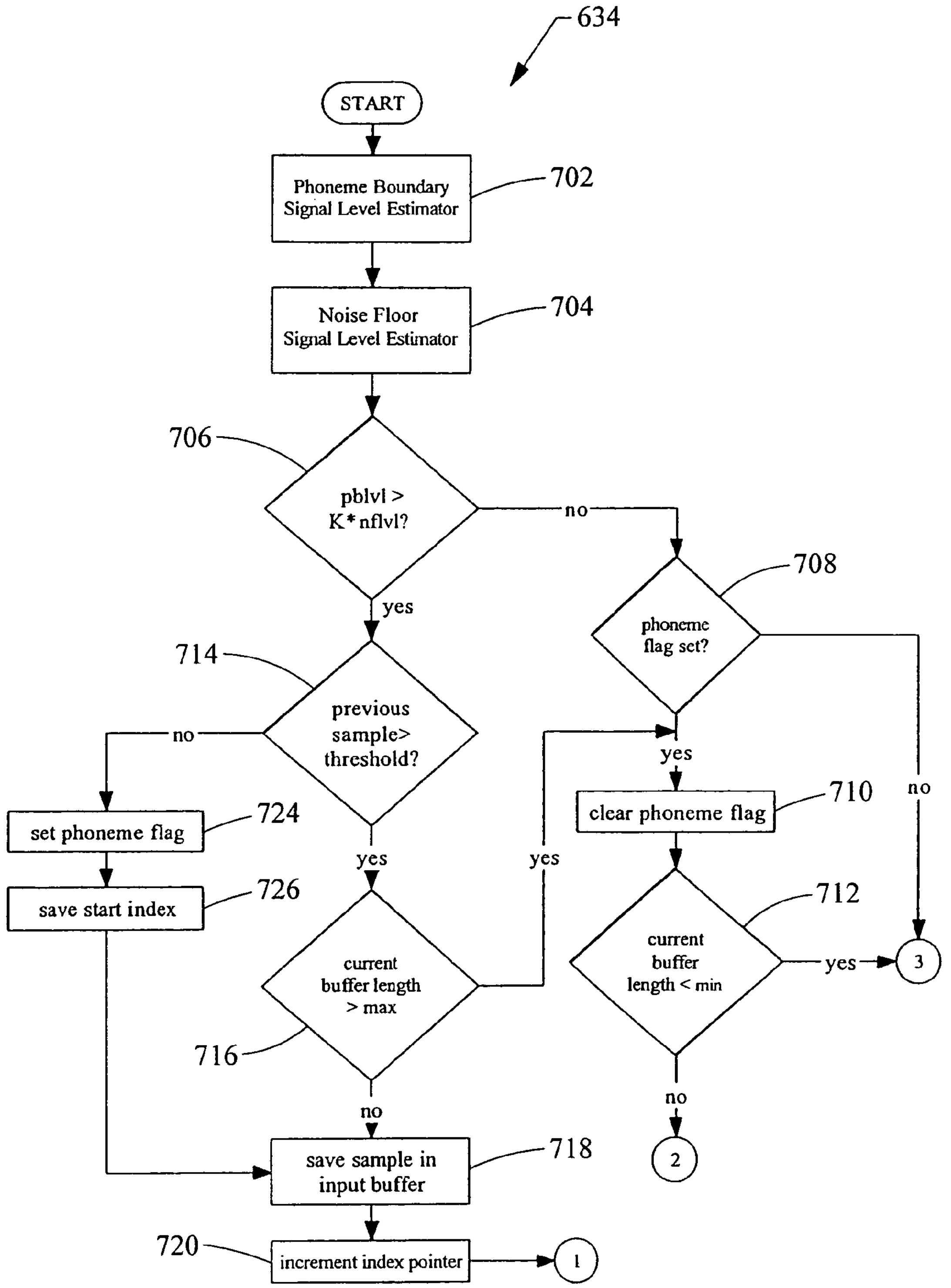
FIGS. 7A-7B is an example of a flow diagram for the input buffer formation depicted in FIG. 6B.
Figure 7B:
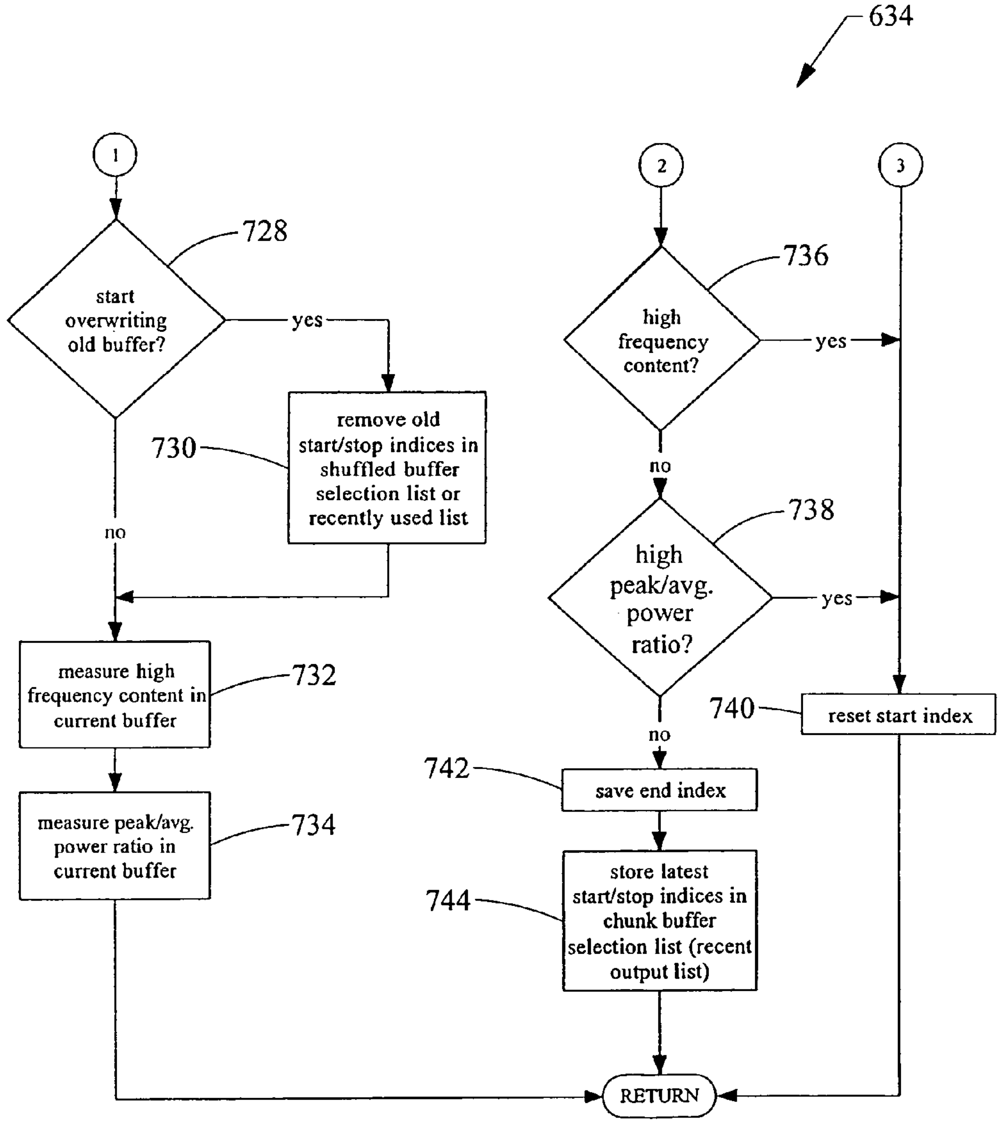

When the talker's voice is in the correct range and the talker feels comfortable that the voice level can be maintained, the talker may activate the top oval button to start recording into the memory and codec provides input from the microphone, as shown at block 630. In this case, the microphone amber LED may become a solid light. Or, the talker may activate other switches to start recording into the memory. The privacy apparatus may monitor the system for a mode switch into a pause mode (block 632) and continues to provide input into the buffer to form the chunks if the privacy apparatus remains active. That is, at any time during the recording the talker can pause entry of the voice into the memory by pressing the top button and pausing the recording. Re-pressing the top button allows the talker to continue entering their voice into the privacy apparatus. When the entry is paused the amber LED light blinks indicating the memory is not yet full. Until the buffer is filled, the input buffer is formed, as shown at block 634. FIGS. 7A-B comprise an example of a flow chart for the input buffer formation 634. During the recording of the talker's voice, the talker's voice need not be emitted from the speakers. When the memory is full, the base unit provides the talker with an auditory indication that the memory is full. The amber microphone and top oval LEDs turn off, also indicating to the talker that the memory is full. When the privacy apparatus is in modes other than the training mode, the microphone LED is off.

To erase the memory, the talker may place the privacy apparatus into training mode and holds the down button down for a predetermined period of time, such as 3 seconds. After this period, an audio beep is heard. After which (such as a period of up to approximately 40 seconds), the memory is empty and the talker begins to determine the voice level. The talker can erase the memory only in training voice mode and when it is erased the amber light by the microphone is activated in a blinking state.

Because talkers may input speech at a variety of loudness levels, with some talkers speaking more softly and other speaking more loudly, the amplitude of the input speech may be modified prior to storage. The modification may occur at the Codec and/or during processing of the input speech. For example, after a speech fragment is identified, as discussed below, the power for the speech fragment may be analyzed. Specifically, if the square of the amplitude of the signal for the speech fragment is either lower or higher than a predetermined range of acceptable power, the amplitude of the speech fragment may be modified. In this manner, the amplitude of the speech fragment may be normalized prior to storage in the input buffer.

As discussed above, incoming speech may be segmented into individual phoneme, diphone, syllable, and/or other like speech fragments. The resulting fragments may be stored contiguously in a large buffer that can hold multiple minutes of speech fragments. A list of indices indicating the beginning and ending of each speech fragment in the buffer is kept for use by the chunk buffer selection routine. In one embodiment, a circular buffer may be used. As discussed above, for multiple users, speech fragments for each of the user may be stored so that the speech fragments are associated with the respective user.

The incoming speech may be segmented using phoneme boundary and word boundary signal level estimators with time constants of approximately 10 ms and 2 s, respectively, in one embodiment. Multiple voices with different temporal characteristics can be created using different sets of time constants, threshold, and minimum/maximum length. The rhythm or pacing of each voice can thus be varied. The beginning/ending of a phoneme is indicated when the phoneme estimator level passes above/below a preset percentage of the word estimator level. In addition, only an identified fragment that has a duration within a desired range (e.g., 50-300 ms) is used in its entirety. If the fragment is below the minimum duration, it may be discarded. If the fragment is above the maximum duration, it may be truncated or discarded. The speech fragment (input sample) may be stored and indexed in a sample index.

Alternatively, instead of storing speech fragments, the input speech may be stored in non-fragmented form. For example, the talker's input may be stored non-fragmented in a memory. In this case, the speech fragments may be generated when the speech fragments are selected or when the speech stream is formed. Or, fragments may not need to be created when generating the disruption output. Specifically, the non-fragmented speech stored in the database may be akin to fragments (such as the talker inputting random, nonsensical sounds) so that outputting the non-fragmented speech provides sufficient disruption.

Further, the memory may store single or multiple speech streams. The speech streams may be based on the talker's input. For example, the talker's input may be fragmented and multiple streams may be generated. For example, a talker may input 2 minutes of speech. This input may be used to generate 90 seconds of speech fragments. The 90 seconds of speech fragments may be concatenated to form a speech stream totaling 90 seconds. As discussed above, additional speech streams may be formed by inserting a delay. For example, a delay of 20 seconds may create additional streams (i.e., a first speech stream begins at time=0 seconds, a second speech stream begins at time=20 seconds, etc.). The generated streams may each be stored separately in the memory. Or the generated streams may be summed and stored. For example, the streams may be combined to form two separate signals. The two signals may then be stored in the database in any format, such as an MP3 format, for play as stereo on a stationary or portable device, such as a cellphone or an portable digital player or other iPod® type device.

As another example, fragments may be generated by selecting predetermined sections of the speech input. Specifically, clips of the speech input may be taken to form the fragments. In a 1 minute speech input, for example, clips ranging from 30 to 300 ms may be taken periodically or randomly from the input. A windowing function may be applied to each clip to smooth the onset and offset transitions (5-20 ms) of the clip. The clips may then be stored as fragments.

Referring to FIGS. 7A-B, there is shown an example of a flow chart for the input buffer formation to segment the incoming speech. In one aspect, the input buffer formation identifies speech fragments with various properties for storage in the input buffer. The speech fragments may later be used to generate the multiple voice streams. As discussed above, one type of speech fragment that may be stored in the input buffer is one that exhibits characteristics of a phoneme. To determine whether the speech fragment comprises a phoneme, a phoneme boundary signal level estimator (pblvl) is used, as shown at block 702. Criteria for determining whether an incoming speech fragment includes a phoneme may comprise the time constant, the threshold, and the minimum and maximum length of the phoneme. For example, the time constant may be set approximately equal to 10 ms. Different criteria may be selected, thereby selecting different sets of phonemes. Further, speech fragments that exhibit characteristics other than a phoneme may be identified.

In order to identify a speech fragment that may exhibit characteristics of a phoneme, the signal level for the speech fragment may be compared with the noise level. For example, the input buffer formation may identify the noise floor signal level estimate (nflvl), as shown at block 704. The noise floor signal level estimate may comprise estimating the background noise in the workspace, such as noise from HVAC. To determine whether a phoneme may be present, the phoneme boundary estimate (pblvl) may be compared with the noise floor estimate (nflvl). As shown at block 706, pblvl is compared to K*nflvl, where K may be a constant equal to 2. If yes, a phoneme may be present in the speech fragment under analysis. Then, it is determined whether the previous sample was greater than a predetermined threshold, as shown at block 714. If yes, it is determined that the speech fragment is in the midst of a phoneme, and the current buffer is checked to see if it is greater than a predetermined maximum, as shown at block 716. One example of a predetermined maximum is approximately 0.4 seconds. Other values may be chosen. If yes, then the speech fragment under analysis is too long for storage in the input buffer. For example, if a talker inputs the speech "Taaaaalk," where the "a" in talk is longer than normally expected, the input buffer formation will not select the "aaaaa" as a speech fragment because it may be outside the maximum allowed phoneme limit. If the current buffer length is less than the predetermined maximum, the speech fragment is saved in the input buffer, as shown at block 718, and the index pointer is incremented, as shown at block 720. If the previous sample is less than the threshold (e.g., the speech may be at the beginning of a phoneme), the phoneme flag is set, as shown at block 724, and the start index is saved, as shown at block 726.

It is determined whether the input buffer should be overwritten, as shown at block 728. There are instances when fragments previously stored in the input buffer are determined to be overwritten. If yes, the start/stop indices in the buffer are removed, thereby removing the speech fragment from the buffer. If not, certain characteristics of the speech fragment at issue are analyzed. As discussed in more detail below, if the speech fragment exhibits certain characteristics, the speech fragment may not be stored in the input buffer. For example, the high frequency content may be measured, as shown at block 732. As another example, the peak/average power ratio is measured, as shown at block 734.

If a phoneme is determined not to be present (pblvl is less than K*nflvl), then it is determined whether the phoneme flag is set, as shown at block 708. If it is set, then this indicates the end of a phoneme and the phoneme flag is cleared, as shown at block 710. Further, the current buffer length is compared with a predetermined minimum, as shown at block 712. An example of a predetermined minimum is approximately 0.1 seconds. If the current buffer length is less than the minimum, then the potential phoneme under analysis may be too short in duration. Thus, the input speech fragment at issue is not stored as a phoneme in the input buffer, and the start index is reset, as shown at block 740. Thus, blocks 712 and 716 ensure that the speech fragments stored are within a predetermined range.

If the current buffer length is greater than the minimum and the end of the speech fragment has been identified, various aspects of the speech fragment at issue may be analyzed. As one example, the high frequency content of the input fragment may be analyzed, as shown at block 736. High frequency content may be indicative of certain types of sounds, such as "sss," which may be undesirable for input to the buffer. Listening tests have shown that people may not appreciate the sound of randomly repeated "sss" phonemes. These sounds have a higher frequency and thus on a graph of amplitude vs. time, a larger number of zero-crossings than other phonemes. Thus, to eliminate such sounds, the number of zero-crossings is calculated in each speech fragment. A large number of zero-crossings indicate the presence of a high frequency noise and the entire fragment is discarded by resetting the input sample index back to a starting index value. Similarly, the ratio of the peak to average power is calculated for each fragment so that segments with extreme peaks can also be discarded. More elaborate chunk analyses may also be performed to tag each chunk with its phoneme and/or syllabic content. This information may be used to optimize privacy performance of the chunk output.

In general, the sound quality of sillibant ('sss') sounds in the privacy apparatus may be undesirable and input chunks that contain the sillibant sounds are detected and discarded. Alternatively, sillibant sounds need not be discarded. Experiments have shown that certain female talkers with relatively large amounts of high frequency content require that sillibant sounds not be removed so as to produce adequate privacy. To accommodate such situations, a sillibant on/off switch may be provided. Or, a sillibant analyzer may automatically adjust the proper amount of sillibant content. Such an analyzer may measure the relative proportion of high frequency, sillibant content in the talker speech and adjusts the sillibance detector threshold accordingly. For example, for relatively low-frequency dominated male speech, the detector threshold may be set to effectively remove all sillibance, while for high-frequency dominated female speech, the threshold may be set to retain all chunks with sillibant content. The amount of sillibant content between these two extremes may be adjusted accordingly.

As another example, the high peak and/or average power ratio of the speech fragment may be analyzed, as shown at block 738. Certain sounds such as clicks (e.g., the clicking of a pen) or plosives may be undesirable for storage in the input buffer. A high peak may indicate such sounds, so that they are not stored in the input buffer, as shown at block 740. If no, the end index is saved, as shown at block 742, and the latest start/stop indices are stored in the input buffer, as shown at block 744.

Figure 6C:
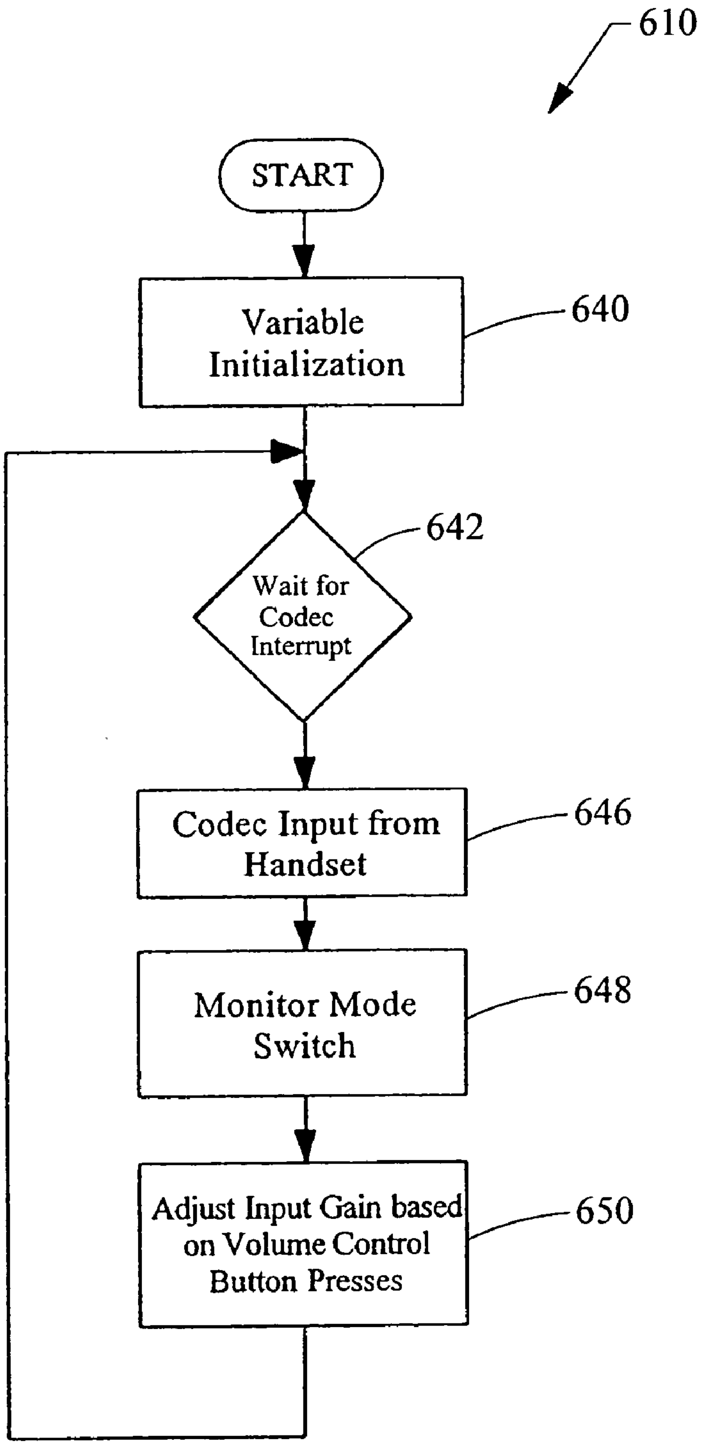

FIG. 6C depicts an example of a flow chart for the input gain adjust mode 610 of the privacy apparatus. Specifically, the talker may set the gain for the input device. As with the other modes, the privacy apparatus initializes the variables when the talker switches the privacy apparatus into the gain setting mode using the three-position switch, as shown at block 640. The top oval light lights up in the lower amber position to signify a new mode. The privacy apparatus waits for the codec interrupt from the handset, as shown at block 642. The talker may place a call using the input device, holding the input device in the normal position when talking on the phone, to initiate the codec interrupt and provide codec input, as shown at block 646. The privacy apparatus may continue to monitor the mode of the system to determine whether the mode has been switched, as shown at block 648, and if not, the input gain may be adjusted, as shown at block 650. While the talker is talking in an appropriate or desired-use voice level, the top oval lights up in the same manner as in the training mode to indicate whether the gain should be adjusted up or down. The talker may then adjust the gain using the up/down buttons until the top oval shows a solid blue center.

Once the correct gain is set for the input device, the talker may switch the privacy apparatus out of gain setting mode to the operation mode to set the speaker volumes. The talker may either place another call or reads from predetermined text. The talker, with help from another person, may adjust the volume of the loudspeakers using the up/down buttons so that the talker has coverage from all desired directions at the lowest possible sound level. When the volume settings are in the minimum or maximum position (in either the operation mode or the gain setting mode), an auditory beep is heard. After volumes are adjusted, the base is rotated back to the upright position and the base and phone are re-positioned as desired on the desktop. In instances where a set of speakers are too loud or placed too close to another co-worker, individual speakers can be adjusted by the talker to change the volume.

Figure 6D:
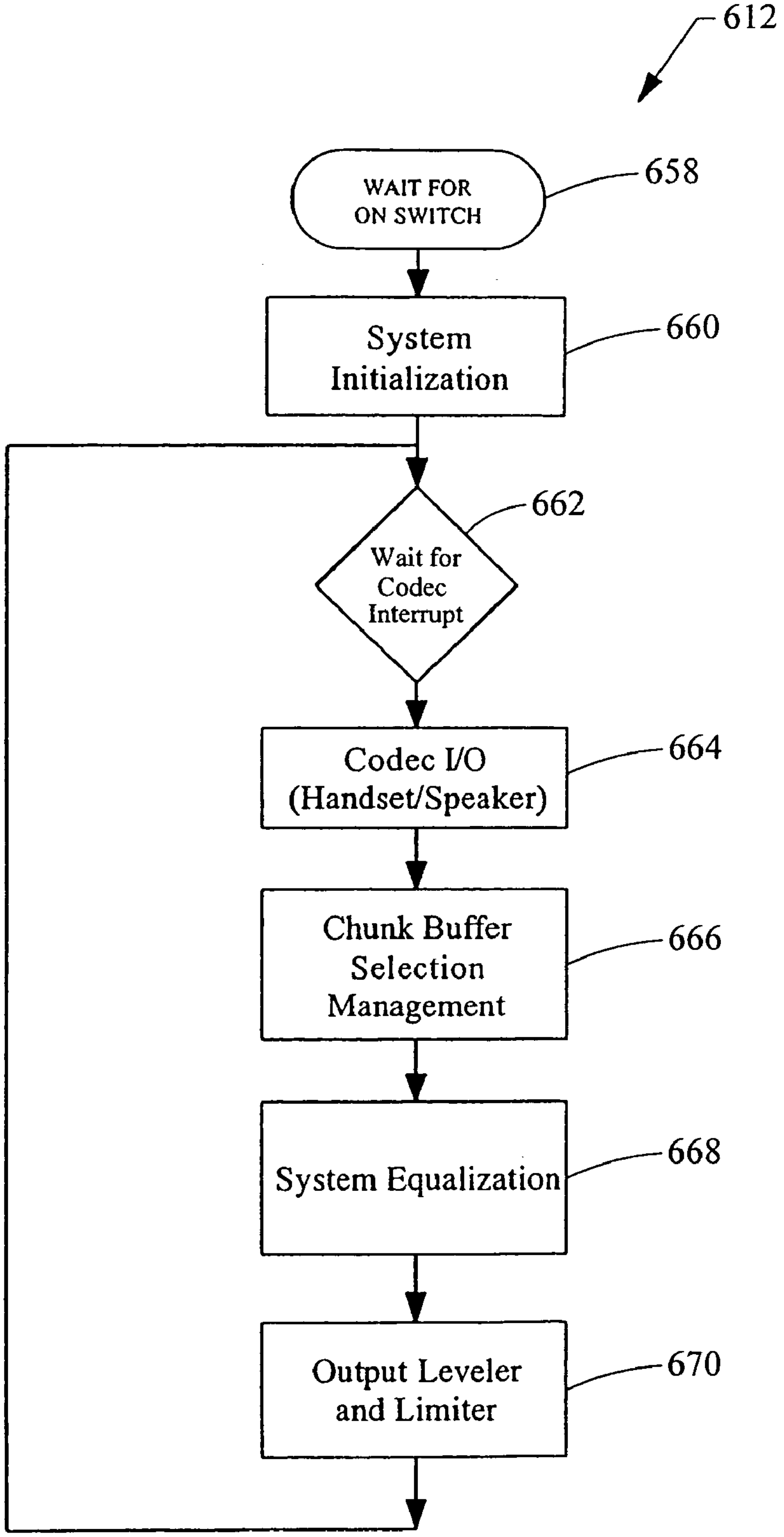

The privacy apparatus may then be operated in use mode. One example of a flow chart for operation of the privacy apparatus in use mode 612 is shown in FIG. 6D. The privacy apparatus, which may sit on a desk behind or around the phone, may first be powered on (block 658) and initialized (block 660). A low level blue glow (for example, about 30% of the maximum intensity) may radiate from the front center icon as well as from the top oval button. The low level output blue light may indicate that power is on to the base but that the use mode is inactive. The privacy apparatus may be activated in a variety of ways. For example, the talker may activate the top button, which leads the low glow on the top and sides to pulse (from high glow to a low glow) and signify that the privacy apparatus is on. In this manner, the talker may manually control the activation of the privacy apparatus, such as when the talker either places or receives a call they wish. Alternatively, the privacy apparatus may automatically activate. For example, the privacy apparatus may automatically sense the presence of sound and begin providing output. Sensing of the sound may be performed in several ways, such as an external sound sensor or such as by monitoring the apparatus associated with the privacy apparatus (e.g., determining whether there is sound being transmitted by the telephone). The automatic sensing of the privacy apparatus may be for a predetermined time (e.g., if after 10 minutes, no sound is generated, the privacy apparatus may turn off).

Figure 8:
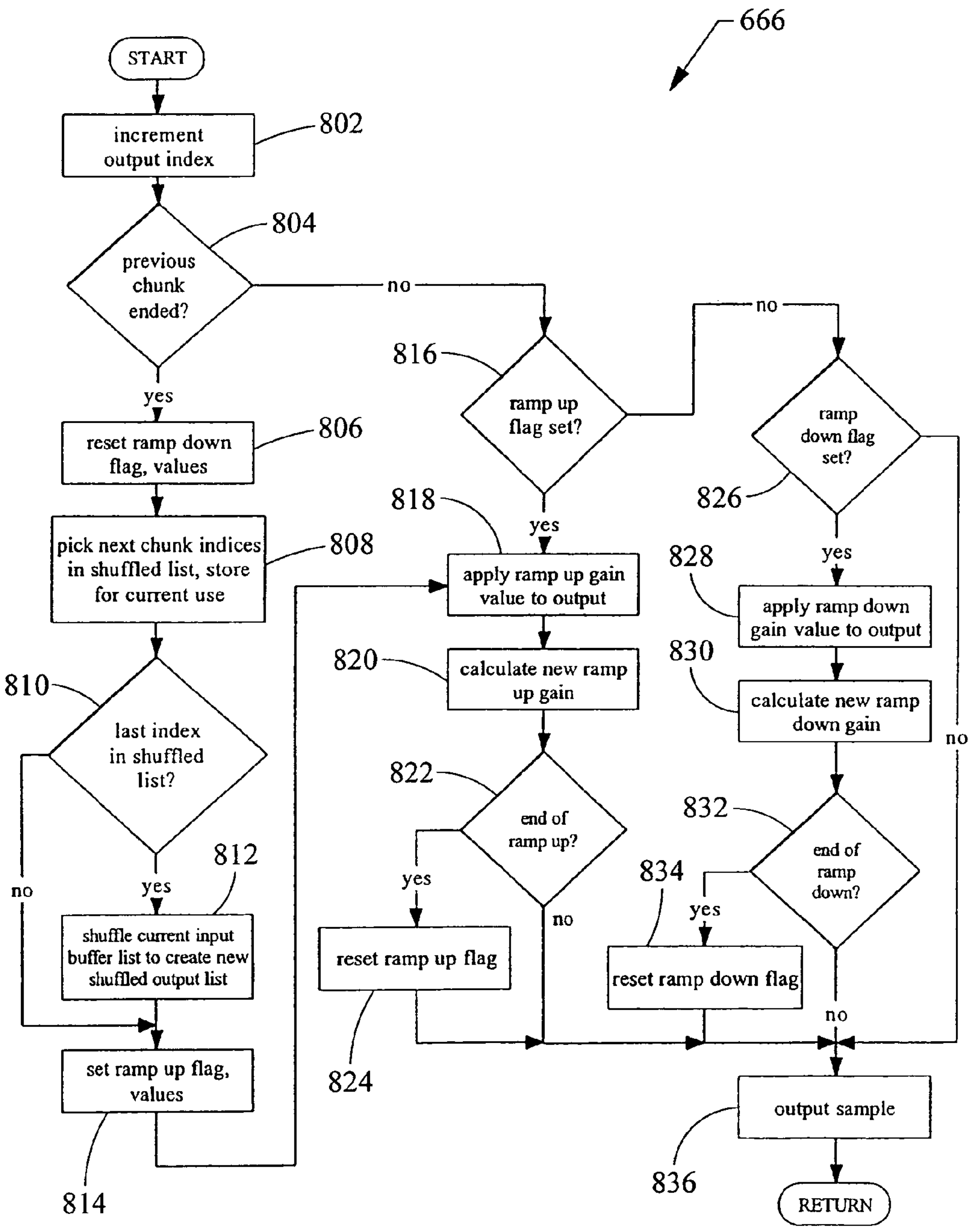
FIG. 8 is an example of a flow diagram for the chunk buffer selection depicted in FIG. 6D.

The codec may again wait for an interrupt from the handset, as shown at block 662. As the talker has their conversation, the blue lights may perform a pulsing animation indicating output is being supplied, i.e., the codec input and output is provided, as shown at block 664. The privacy apparatus may select random overlapping chunks (multiple random voices) from the memory (block 666), equalize the system and levels (block 668) and limit the output to the loudspeakers (block 670). FIG. 8 is an example of a flow chart for the selection of the chunks.

If the conversation gets louder than the level of coverage the privacy apparatus provides, then both ends of the oval may turn solid amber (in the default mode setting) while the center continues to pulse. If the talker changes from the default limit mode to a no-limit mode, the privacy sound will rise with their voice without limit. In this no-limit mode, both ends of the oval may turn solid amber when the talker exceeds the limit point even though the privacy sound continues to follow and output. This is an indication to the talker that he or she is talking above a defined reasonable level. Alternatively, the privacy apparatus may include a series of LEDs or other visual indicator to indicate to the talker the talker's level of speech. For example, the visual indicator may indicate whether the talker's level of speech is acceptable, loud, or too loud. In this manner, the visual indicator may indicate to the talker whether the speech is too loud for the talker to lower his or her speech manually.

The de-activation of the privacy apparatus may be manual or may be automatic. Specifically, the talker may manually deactivate the privacy apparatus. For example, when the call is ended, the talker may turn off the privacy apparatus by de-activating the top oval button. The intense blue light or animation is replaced by the original low blue glow. Alternately, when the call is ended, the talker places the phone down without de-activating the privacy apparatus. The privacy sound may stop animating when the conversation stops and the privacy sound may no longer be emitted from the privacy apparatus (e.g., the privacy apparatus emits a privacy sound for 3 to 4 minutes after the last sound of the talker is sensed by the privacy apparatus). The blue light may pulse when the privacy apparatus emits a privacy sound.

A light pipe may also surround a front logo on the base. Both the blue light on the top oval and the blue light from the edge around the button on the front logo thus react in the same manner during the different modes. For example, the light pipe surrounding the front logo glows low blue indicating that power is being supplied to the privacy apparatus. The light pipe glows with a high intensity blue when the privacy apparatus is turned on and pulses to indicate that output is being supplied by the privacy apparatus.

A random speech fragment output may be formed by randomly shuffling the list of input speech fragment indices from which to select a speech fragment for output. Other methods of choosing chunks to output can be utilized to optimize privacy performance. Input fragment indices may also be removed by the input formation routine as input fragments are overwritten in the buffer. Alternatively, rather than attempt to breakup the incoming speech into fragments on phoneme or syllable boundaries, active speech input chunks of random duration (with a known mean and range) may be formed, insuring that each randomly formed chunk is adequately ramped up/down to eliminate abrupt transitions between chunks.

Because random speech fragment output may constantly be chosen to play, the output stream may constantly change. In this manner, there is less opportunity of noticing a repeating of the output. Therefore, with a relatively small, low cost memory, a steady stream of new output may be apparently produced. However, the output derives from a small actual buffer of recorded speech fragments. A minimum amount of speech fragments may be used to provide a sufficient diversity of chunks to create the apparent non-repeating stream. This minimum amount may be about 30 seconds, or may be longer or shorter than 30 seconds.

As each speech fragment is supplied to the output, a starting ramp on and ending ramp off envelope may be applied to minimize abrupt transitions between speech fragments. The shape of the envelopes may be exponential (constant dB) and last approximately 20 ms. If multiple (such as two to five) separate audio streams are desired, the streams may be supplied in parallel to the output and each stream may share the same circular buffer and randomized begin/end indices list.

In one embodiment, the input buffer is already filled with speech fragments via the training mode. In another embodiment, once in the operation mode, the output selection routine waits for the input buffer to fill up to a minimum number of chunks prior to starting to output samples. In this manner, the input buffer may be filled in real-time or just prior to generating voice streams for output. The input buffer formation routine may be partly or fully executed first, and then the chunk output selection routine may be executed. In addition, when a new speech fragment is selected, the end index may be saved in a temporary location so that it is not removed by the input buffer routine if it starts overwriting the current buffer being output. These actions may prevent overwriting samples in a current output buffer when earlier samples in the buffer are currently being overwritten by the input buffer.

Referring to FIG. 8, there is shown an example of a flow chart for selection of the speech fragments depicted in block 666 of FIG. 6D whereby the input buffer is already filled with speech fragments via a training mode. Further, the flow chart depicts the processing for one voice stream. Various portions of speech of the talker, such as the talker's speech fragments, may be concatenated together to generate a single voice stream. Additional voice streams, such as 2-5 voice streams, may be generated. The same algorithm may be implemented for the multiple voice streams, with the only difference being that multiple indices may be processed with each pass. To maximize the duration between repeating a given speech fragment output, the indices for each voice may be maximally spaced across the shuffled output list whenever a new shuffled list is started. The separate voice streams may then be summed and output.

The voice streams may comprise a steady stream of speech fragments, whereby a part or all of the voice stream is composed of speech fragments without any audible gaps in between the speech fragments. Alternatively, in addition to selecting various portions of the talker's speech to generate the voice streams, gaps or sections without speech may also be inserted. For example, gaps of a predetermined duration (e.g., 50 ms) may be inserted between some or all of the speech fragments selected. Or, gaps of variable duration may be inserted between some or all of the speech fragments selected. For example, a predetermined range of gaps may be defined (e.g., 30 to 70 ms) and the gaps may be randomly selected within the predetermined range. Using gaps in forming the voice stream may be beneficial in several respects. First, using gaps may lower the amplitude of the voice stream. Because 2, 3 or more voice streams may be summed for output on a single channel, gaps may lower the summed amplitude of the voice streams. Second, using gaps may more accurately reflect a real-life voice stream that naturally includes gaps.

As shown at block 802, the output index is incremented. The output index may point to a list of randomized speech fragments. It is determined if the previous speech fragment has ended, as shown at block 804. If so, the ramp down flag is reset (block 806) for a smooth transition on the output, as discussed above. The next speech fragment is selected from the shuffled list, as shown at block 808. If the selected speech fragment is the last index in the shuffled list (block 810), then the buffer input list is re-shuffled to create a new shuffled output list, as shown at block 812. For a smooth transition for the new speech fragment, the ramp up flag is set, as shown at block 814.

If the previous speech fragment has not ended (block 804), then it is determined whether to ramp up the output for the speech fragment, as shown at block 816. If yes, the output of the speech fragment is ramped upward by applying the "ramp up gain" to the output (block 818), and calculating a new "ramp up gain" (block 820). If the new ramp up gain is at the maximum (i.e., at the end of the ramp up, as shown at block 822), then the ramp up is completed and the ramp up flag is reset, as shown at block 824.

It is also determined whether to ramp down the output of the speech fragment by checking whether the ramp down flag has been set, as shown at block 826. If yes, the output of the speech fragment is ramped downward by applying the "ramp down gain" to the output (block 828), and calculating a new "ramp down gain" (block 830). If the new ramp down gain is at the minimum (i.e., at the end of the ramp down, as shown at block 832), then the ramp down is completed and the ramp down flag is reset, as shown at block 834. The speech fragment is then output, as shown at block 836.

While FIG. 8 depicts ramping the speech fragment output sample upward and downward for smooth transition between speech fragments, the speech fragments may be shaped prior to storage in the buffer so that they may simply be output without requiring shaping (e.g., ramping upward and downward) prior to output.

In an alternative embodiment, once the chunk buffer is filled, the privacy apparatus may switch into operation mode in which an automatic gain control and formation processes are disabled. In this case, the privacy apparatus may continuously or periodically update the chunk buffer to new speech input. For example, the telephone handset microphone may input speech to the privacy apparatus and create a constantly updating collection of voice chunks in a SDRAM memory for playback. Thus, unlike the apparatus discussed above, the memory may be updated with further use after the initial training rather than relying on stored speech as the source of the privacy sound. However, unlike the built-in microphone on the base of the privacy apparatus, which has sufficient frequency response to recreate near life-like speech sound, many wireless headsets and wired headset devices commonly in use do not provide good quality speech input.

Turning from the operation of the base unit of the privacy apparatus to the loudspeakers, each loudspeaker may contain two separate sound drivers that are positioned (aimed) 120 degrees apart. This 120-degree alignment may provide near uniform frequency response coverage on the front 180 degrees of the loudspeaker. Each driver may receive one channel of the 2-channel output from the privacy apparatus. The 2-channel output need not be stereo but may be two different streams of privacy sound produced from a random arrangement of the voice segments from a bank of voice segments stored in non-volatile memory. Each channel may be a different compilation of 2-5 voice streams so that the output of each driver is never the same. This permits the two drivers to be provided in the same loudspeaker housing and share the same "back volume." Sharing the same back volume permits a significantly smaller loudspeaker design that produces a near uniform 180-degree output of privacy sound. The directionality limitation of normal loudspeakers is overcome thus providing wide-angle coverage from a single source. Alternatively, the loudspeaker may contain 3 or more separate drivers and output 3 or more channels.

Each loudspeaker may have a 2-channel amplifier, two 6-conductor RJ11 style jacks (signal & dc power in/signal & dc power out), and a volume control that allows for adjusting the loudspeaker units output volume (both drivers). An optional blue LED power indicator light may be added to the back of the loudspeaker to show that the loudspeaker is properly connected.

The cabling that connects the loudspeakers to the base of the privacy apparatus and each other may be commonly available 6-conductor phone line cable with RJ11 connectors on each end. The base unit may provide dc power on two of the conductors and there are two conductors for carrying each of the two signal channels. The signals need not be amplified to drive the loudspeakers; instead, each loudspeaker may use the dc power provided to drive its own 2-channel amplifier that amplifies the supplied signal to drive the two loudspeaker drivers. The dc power and both signals may be passed onto multiple other loudspeaker units in a "daisy chain" connection scheme. Therefore, while there are only two loudspeaker connection jacks on the main unit, additional loudspeakers may be added to the system via "daisy chain" connections to other loudspeakers. This connection approach allows for having a single cable coming to a loudspeaker unit that provides both power and 2 signals. Connecting sequential loudspeakers reduces the installation difficulty and wire management problems of having to bring a cable from each loudspeaker back to the main unit.

The LEDs and controls on the loudspeakers include a volume control that allows the talker to adjust the volume of each speaker set individually and an LED that indicates power is on to the loudspeaker. The volume control is located under the speaker.

After the output chunk is selected, the system is equalized, as shown at block 668 of FIG. 6*d*. The equalization filter may shape the overall spectrum of the output to compensate for the system, including microphone and loudspeaker responses, and to optimize privacy performance, system directivity, and sound quality. The output leveler, shown at block 670, may then vary the output level so as to track the level variations of the person speaking by applying a gain factor to the output samples that is proportional to a measurement of the input level. The variation of the gain is controlled by a relatively long time constant (1-5 s). The entire system output may be gradually muted if no input signal is detected for an extended period and turned back on when input speech is detected.

The output leveler may provide a sufficient privacy level at the listener's location. It may also be desirable to minimize the output level so as to insure the overall acceptance of this technology in the office environment. Accordingly, an output level indicator such as the LEDs may encourage talkers to keep their voice at a lower level. The indicator can indicate to the person speaking that they are speaking too loudly and recommend that the speaker lower their voice to insure privacy, even though the leveler may actually be providing adequate privacy. Thus, both adequate privacy and minimization of the sound level in the office environment can be provided.

The output leveler described above may have a 1:1 relationship with the input level of the person speaking. That is, for every dB variation in average input level, the output leveler produces a corresponding dB change in the average output level (with suitable time constants). However, it may not be desirable to allow the system to output levels to overcome a person who is shouting or otherwise speaking in a loud voice. One alternative to this situation is to put a maximum limit on the 1:1 input/output level relationship such that, above a certain defined level, the output level no longer increases, or increases at a much slower rate, with further increases in person speaking input level. This also works in conjunction with the output level indicator described above to inform the person speaking that they are no longer obtaining privacy and to suggest they lower their voice.

During the training mode of the privacy apparatus, the output level may be manually adjusted while speaking until a listener at the listener's position indicates that they can no longer comprehend what they are saying. Alternatively, a remote wired or wireless microphone system attached to the privacy apparatus that the loudspeaker carries into the listener environments is used to measure the output level. This information along with the average input level of the person speaking is then used to obtain the proper output level without the need for a listener's assistance. The remote microphone system may be used to equalize the system output in the listener environment.

The privacy apparatus may initially be put into the training mode in which a person reads prepared test sentences into the microphone on the top of the base until the chunk buffer is filled. Once the chunk buffer is filled, the privacy apparatus is switched into the gain adjust mode. Once the gain of the input device being used has been adjusted for, the chunk buffer is then switched into the operation mode and used as desired for conversations. The chunk buffer is sufficiently long such that the repetitive use of the chunk buffer is not noticed by listeners. It may also be desirable in certain environments to sum a low-level random noise into the output to provide additional privacy between the gaps of the privacy apparatus. It is also possible that a more intelligent selection of output chunks (rather than random) may be performed to maximize privacy apparatus performance and/or sound quality. For example, a well-distributed use of a variety of phoneme types can be insured. In addition, a more natural temporal structure of vowel-consonant streams can be created. Such processes can be facilitated by tagging each input chunk and/or sorting them into sub-categories within the chunk buffer.

The privacy apparatus may output one voice stream or multiple voice streams (or "voices") in parallel. These voice streams may be created using the entire chunk buffer. However, by varying the properties of each voice, the sound quality and privacy performance can be improved. As mentioned above, one variation may be to create input chunks with different rhythmic properties that are stored in different chunk buffers.

In another embodiment, chunk buffers that contain voices from other people may be pre-stored and mixed in as other voices. For example, speech (such as speech fragments) may be stored for people other than the talker whose speech is emanating from the workspace. The speech of the other people may represent a cross-section of different types of voices, such as male and female voices (e.g., one set of speech fragments for a male age 15-20; a second set of speech fragments for female age 15-20; a third set of speech fragments for male age 20-25; etc.), husky or soft voices, different accent voices, etc. These other voices may be used to create a single or multiple voice streams. Or, these other voices may be used in combination with the speech of the talker, such as generating voice streams based on the speech fragments of the talker and voice streams based on the speech fragments of people other than the talker. The generated voice streams based on the speech fragments of the talker and voice streams based on the speech fragments of people other than the talker may be summed together and then output. Or, the generated voice streams based on the speech fragments of the talker may be summed and output on one channel and the generated voice streams based on the speech fragments of people other than the talker may be summed together and then output on a second channel.

FIG. 9 shows another example of a flow diagram for the input buffer storage and multiple voice stream generation from the stored input buffer. The microphone input 902 may be transmitted to the codec 904, where the input is filtered and A/D converted 904*a*. The filtered and converted signal may be buffered through input buffers 906 and the output from the buffers 906 may be supplied to a manual gain 908. The manual gain 908 may apply a particular amount of gain 910. The signal that was adjusted by the manual gain 608 may then be filtered with high-pass filters 912. The high-pass filtered signal may then be supplied to a conditioned buffer 914 and a raw output buffer 918. The energy of the signal from the conditioned buffer 914 may be calculated 916 as well as supplied to a buffer 920 in which the signal may be analyzed. The high frequency of the signal may be analyzed 920*a*, and the peaks detected 920*b*. Further, the automatic gain control (AGC) may be used as described above 920*c*, and the signal may be smoothed 920*d*. The output from the buffer 920 may be supplied to a data interface 922 which communicates with external memory 924 and after which, the output from the data interface 922 and the number of chunks stored 926 may be input to the buffer output algorithm 928. This output may also be supplied to the raw output buffer 918. The output leveler 932 may then apply an output gain 930 dependent on the level of the input to the combination from the raw output buffer 918. A soft limit 934 may then be applied to the output whose gain has been adjusted and the system may be equalized 936 and supplied to an output buffer 938. The signal from the output buffer 938 may be supplied to the D/A converter 904*b* in the codec 904, along with the output control volume 940, which may be adjusted through a user interface 942. The user interface 942 may accept inputs from various buttons 948. The signal from the D/A converter 904*b* may be supplied to speakers 952. In addition, the system may communicate with a PC 950 through a Universal Asynchronous Receiver/Transmitter (UART) interface 944 and/or an RS232 serial port cable. The system may contain an operating system 946 that controls the sequence of events, real time requirements, manages the buffers, provides the input and output device and external memory drivers, and provides a math unit for example. Other processes may not be shown for clarity in the figure.

The privacy apparatus may be used to disrupt speech for a single talker or multiple talkers. The multiple talkers may be speaking concurrently (such as a conversation between two people in the same office) or may be speaking serially (such as a first talker speaking in an office, leaving the office, and a second talker entering the office and speaking). In a concurrent conversation, voice streams for any number of talkers, including 2, 3, 4 or more talkers, may be generated. The voice streams generated may be based on which of the talkers is currently speaking (e.g., the system senses which of the talkers is currently talking and generates voice streams for the current talker). Or, in a concurrent conversation, the voice streams may be based on all the talkers to the conversation (e.g. the voice streams generated are based on speech fragments from all of the talkers to the conversation regardless of who is currently talking). Or, in a concurrent conversation, the voice streams may be based on some, but not all, of the talkers to the conversation. For example, in a conversation between Person A and Person B, the multiple voice streams may initially be based on speech fragments from Person A, and after a predetermined time, may be based on speech fragments from Person B, thereby switching back and forth between the persons to the conversation.

Figure 10:
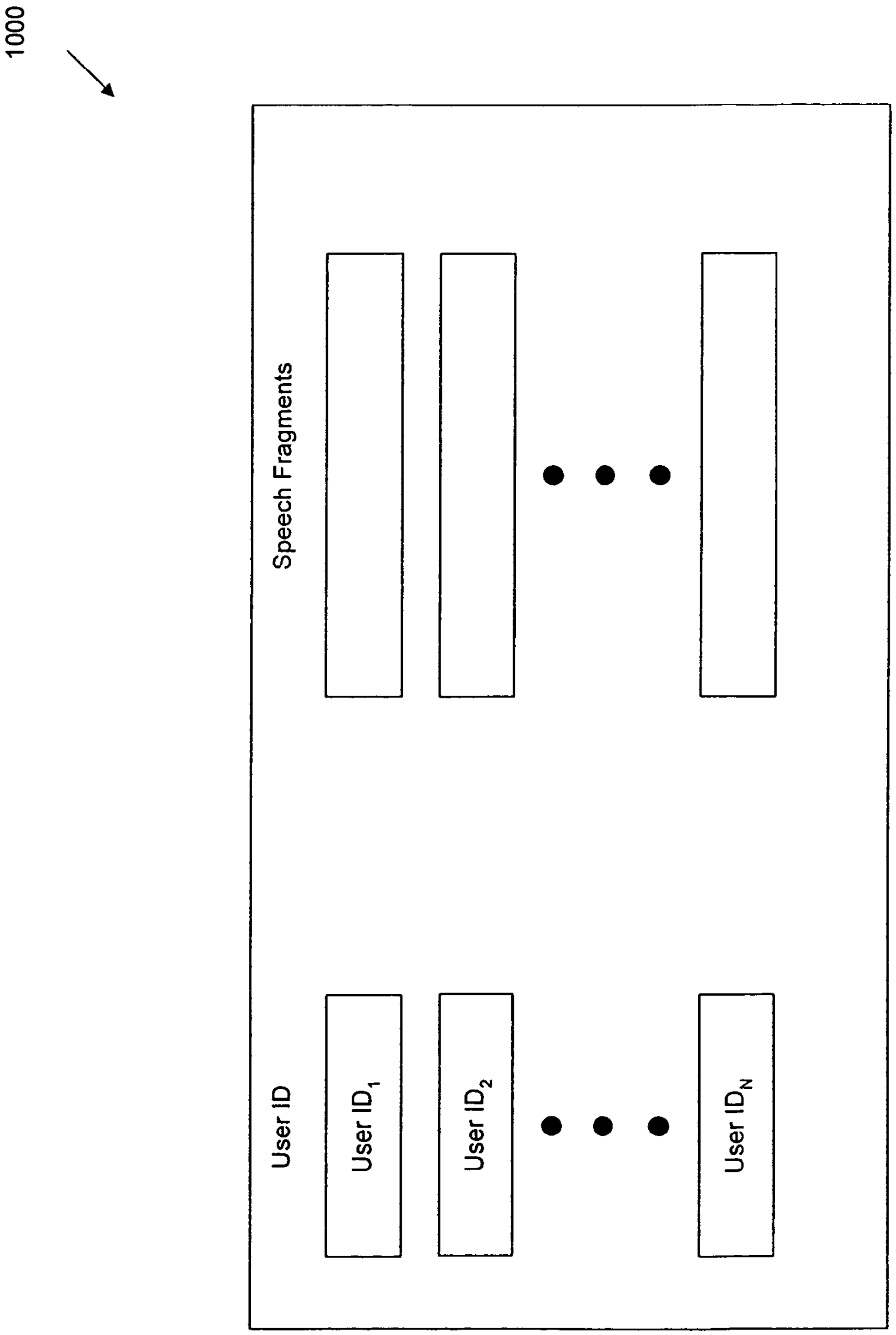
FIG. 10 depicts an example of a memory that correlates talkers with the talkers' speech fragments.

In a multi-user system, the speech fragment database may include speech fragments for a plurality of users. The database may be resident locally on the system (as part of a standalone system) or may be a network database (as part of a distributed system). A modified speech fragment database 1000 for multiple users is depicted in FIG. 10. As shown, there are several sets of speech fragments. Correlated with each speech fragment is a user identification (ID). For example, User $ID_1$ may be a number and/or set of characters identifying "John Doe." Thus, the speech fragments for a specific user may be stored and tagged for later use.

Figure 11:
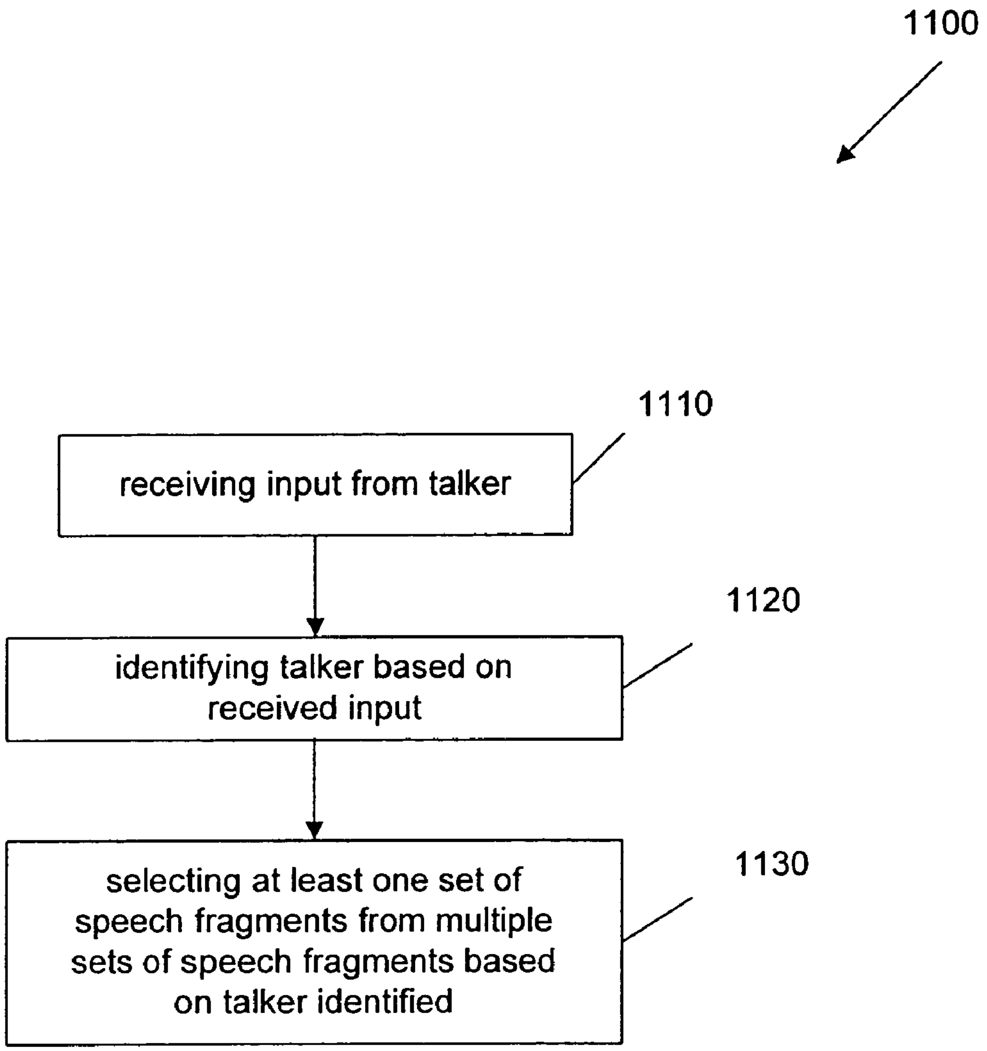
FIG. 11 is an example of a flow diagram for selecting speech fragments in a multi-talker system where the talkers speak serially.

As discussed above, the privacy apparatus may be used for multiple users speaking serially or multiple users speaking simultaneously. Referring to FIG. 11, there is shown one example of a flow diagram 1100 for selecting speech fragments in a multi-talker system where the talkers speak serially. The speech fragment database may include multiple sets of speech fragments, as depicted in FIG. 10. This may account for multiple potential talkers who may use the system. As shown at block 1110, the input is received from the talker. The input may be in various forms, including automatic (such as an RFID tag, Bluetooth connection, WI-FI, etc.) and manual (such as a voice input from the talker, a keypad input, a switch input (e.g., switch 1 for person 1; switch 2 for person 2), or a thumbdrive input, etc.). Based on the input, the talker may be identified by the system, as shown at block 1120. Then, at least one set of speech fragments may be selected from multiple sets of speech fragments based on the talker identified, as shown at block 1130. For example, the talker's voice may be analyzed to determine that he is John Doe. As another example, the talker may wear an RFID device that sends a tag. The tag may be used as a User ID (as depicted in FIG. 10) to identify the talker. In this manner, a first talker may enter an office, engage the system in order to identify the first talker, and the system may select speech fragments for the first talker. A second talker may thereafter enter the same or a different office, engage the system in order to identify the second talker, and select speech fragments for the second talker.

Figure 12:
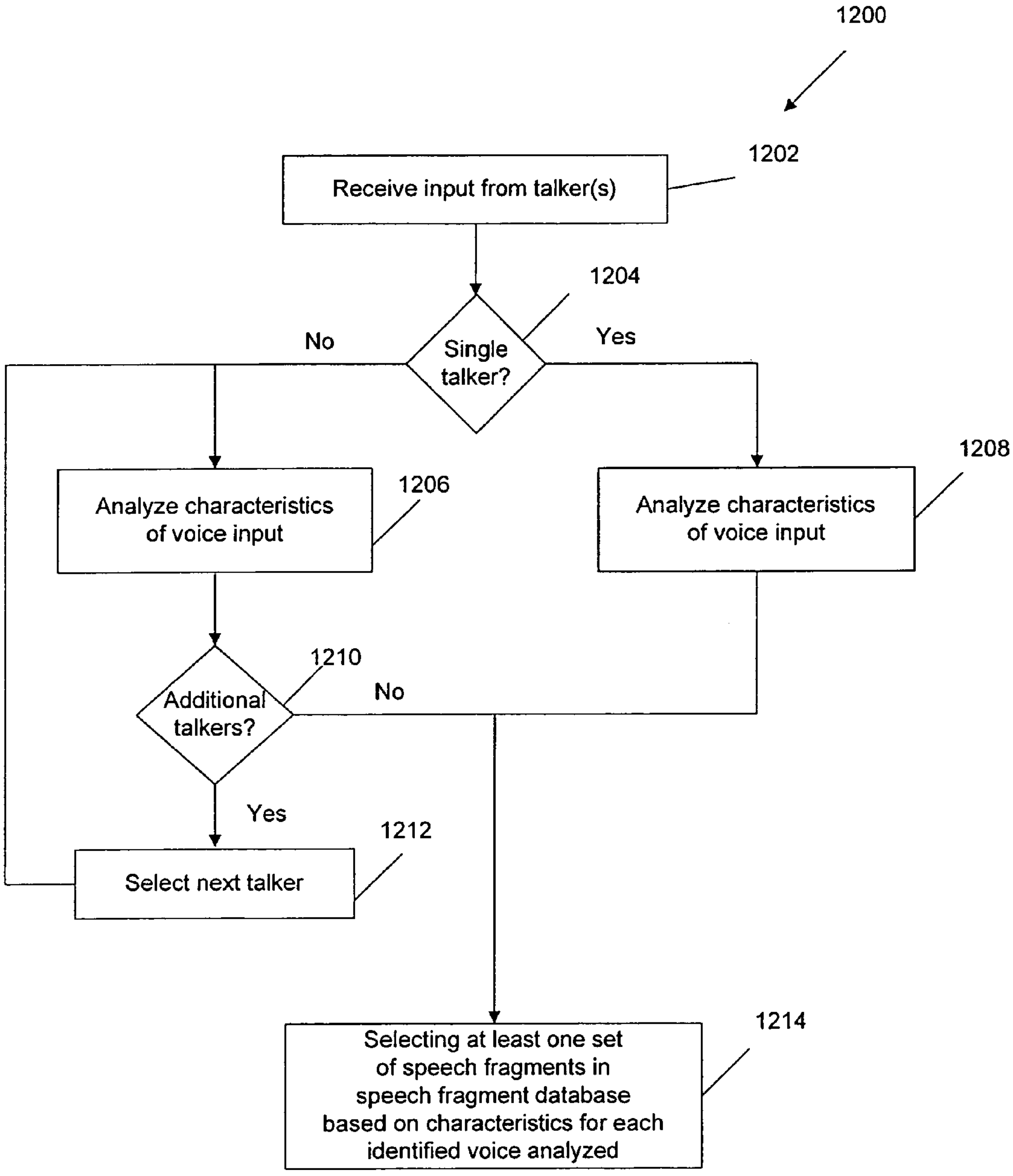
FIG. 12 is an example of a flow diagram for selecting speech fragments in a multi-talker privacy apparatus where the talkers are engaged in a conversation.

Referring to FIG. 12, there is shown another example of a flow diagram 1200 for selecting speech fragments in a multi-talker privacy apparatus where there are potentially simultaneous talkers, such as talkers engaged in a conversation. As shown at block 1202, input is received from one or more talkers. As shown at block 1204, the privacy apparatus determines whether there is a single talker or multiple talkers. This may be performed in a variety of ways. As one example, the privacy apparatus may analyze the speech including whether there are multiple fundamental frequencies to determine if there are multiple talkers. As another example, the privacy apparatus may determine whether there are multiple inputs, such as from multiple automatic input (e.g., multiple RFID tags received) or multiple manual input (e.g., multiple thumb-drives received, keypad input, or multi-position switch input). For either a single or multiple talker, the characteristics of the voice input may be analyzed, as shown at blocks 1206 and 1208. Further, it may be determined whether there are additional talkers, as shown at block 1210, and if so, the next talker is selected, as shown at block 1212. Then, at least one set of speech fragments may be selected from multiple sets of speech fragments based on each talker identified, as shown at block 1214.

Figure 13:
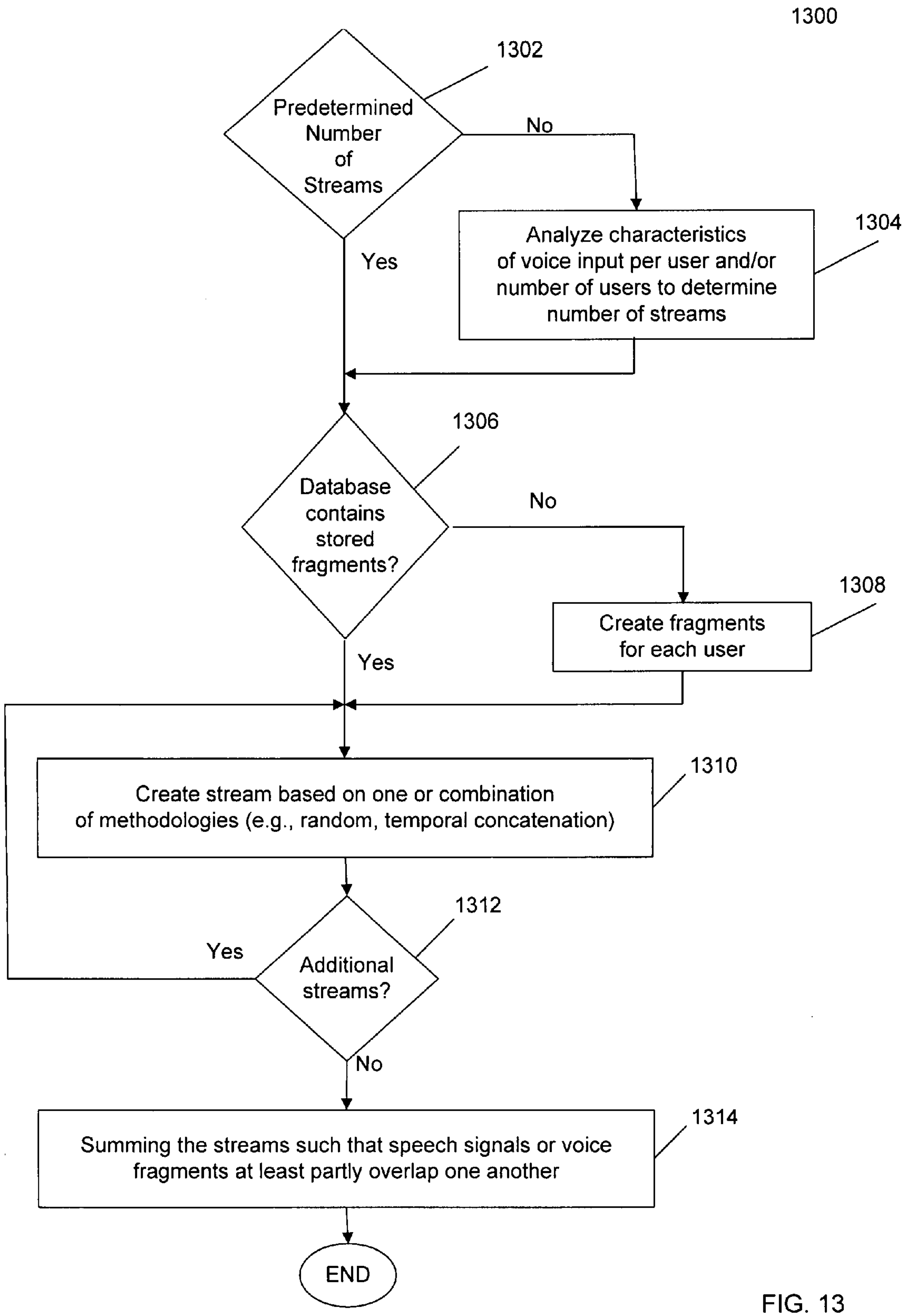
FIG. 13 is an example of a flow diagram of a speech stream formation for multiple talkers.

Referring to FIG. 13, there is shown a flow chart 1300 of an example of a speech stream formation for multiple talkers. As shown at block 1302, it is determined whether there are a predetermined number of streams. If there are not a predetermined number of streams, the voice input may be analyzed for each talker and/or for the number of talkers in order to determine the number of streams, as shown at block 1304. Further, it may be determined whether the database contains stored fragments, as shown at block 1306. In the event the database contains non-fragmented speech, the fragments may be created in real-time, as shown at block 1308. As discussed above, fragmenting the speech may not be necessary. Further, the stream may be created based on one or a combination of methodologies, such as random, temporal concatenation, as shown at block 1310. Alternatively, the system does not need to create fragments, such as if the talker's input is sufficiently fragmented. Finally, it is determined whether there are additional streams to create, as shown at block 1312. If so, the logic loops back. As shown at block 1314, the streams are summed such that speech signals or voice fragments from the streams at least partly overlap one another. As discussed above, the creation of the streams may not be necessary.

To sense the multiple talkers such as described in block 1304, one or more microphones may be used. Any type of microphone may be used, such as a boom microphone, headset microphone, or an omnidirectional microphone. For example, two microphones may be used for a two-person conversation, whereby the microphones may input speech to the base unit for each of the talkers. The input speech may be used for the training as well as use modes. For example, during the use mode, the loudness of each of the speakers may be determined from the speech input to each of the microphones. The amplitude of voice streams output may be modified based on one or both of the input from the microphones. Specifically, the amplitude of the voice streams output may be based on which input from the microphones is higher. The higher input may then dictate the output.

Further, the voice streams used for output on the loudspeakers may remain constant or may vary. For example, in a two-channel output (channel A and channel B) to the loudspeakers, each of the channels may be composed of voice streams based on speech from each of the talkers. Channel A may be a combination of one or more voice streams from Person A and one or more voice streams from Person B, and Channel B may be a combination of a different one or more voice streams from Person A and a different one or more voice streams from Person B. Alternatively, the voice streams used for Channel A and Channel B may alternate between being based on speech fragments from Person A and speech fragments from Person B, as discussed above. The alternation between Person A and Person B may be predetermined (e.g., every 2 seconds alternate) or may be based on which person is speaking (e.g., sensing based on the characteristics of the speech which person is speaking).

FIG. 1 depicts the privacy apparatus used in combination with a conventional telephone. Alternatively, the privacy apparatus may be used in combination with a speaker phone. The microphone associated with the speaker phone may be used both for speech input in the training mode and for voice stream output in the use mode. The speech input in the training mode may obtain speech for the talker speaking in his or her workspace and the talker remote from the speakerphone. Further, any concerns regarding the quality of the microphone to record the input speech is offset by the lower quality of the speech generated by the loudspeaker used in the speakerphone.

Figure 14:
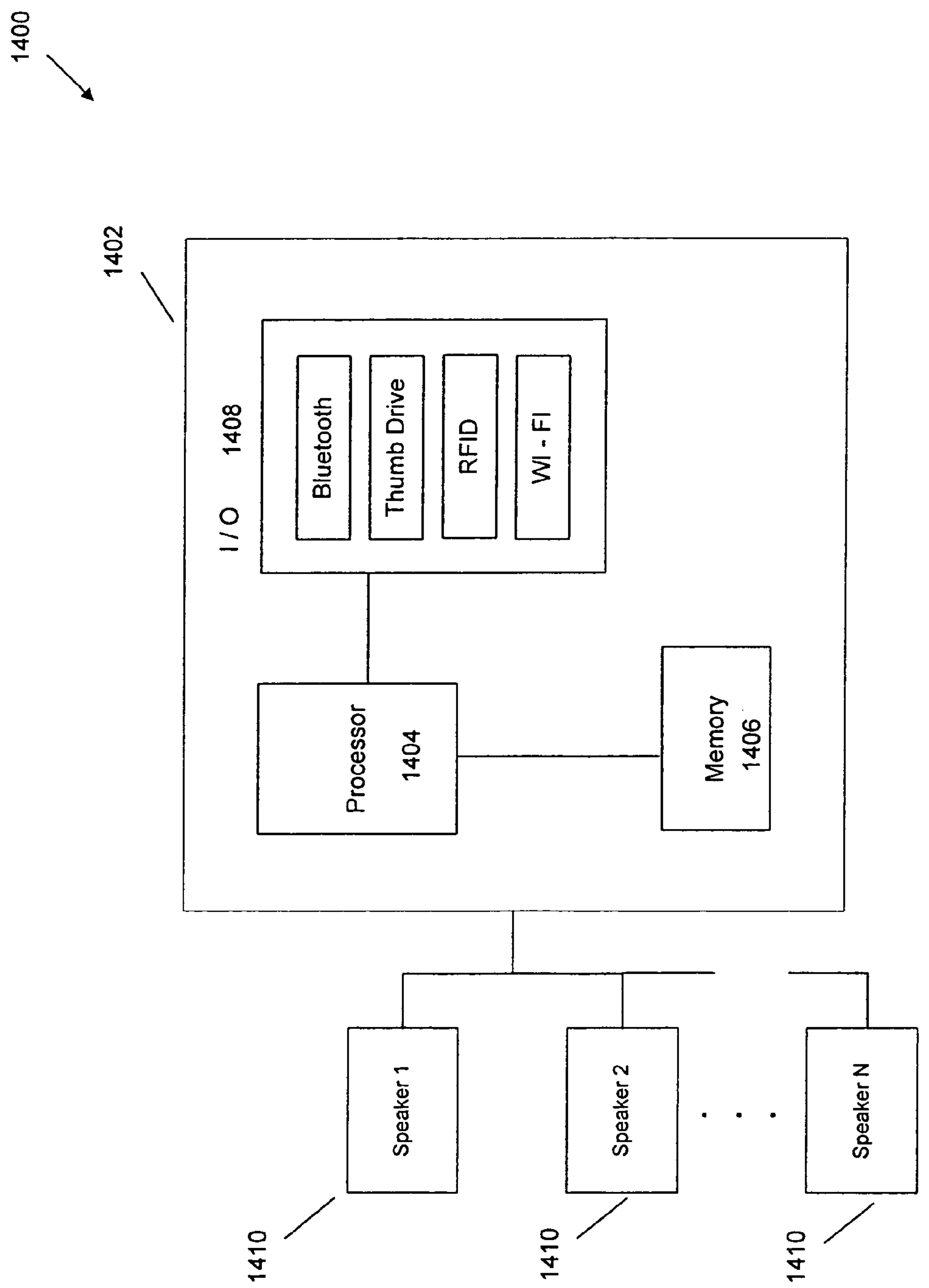
FIG. 14 is an example of a block diagram of a privacy apparatus that is configured as a standalone system.
Figure 15:
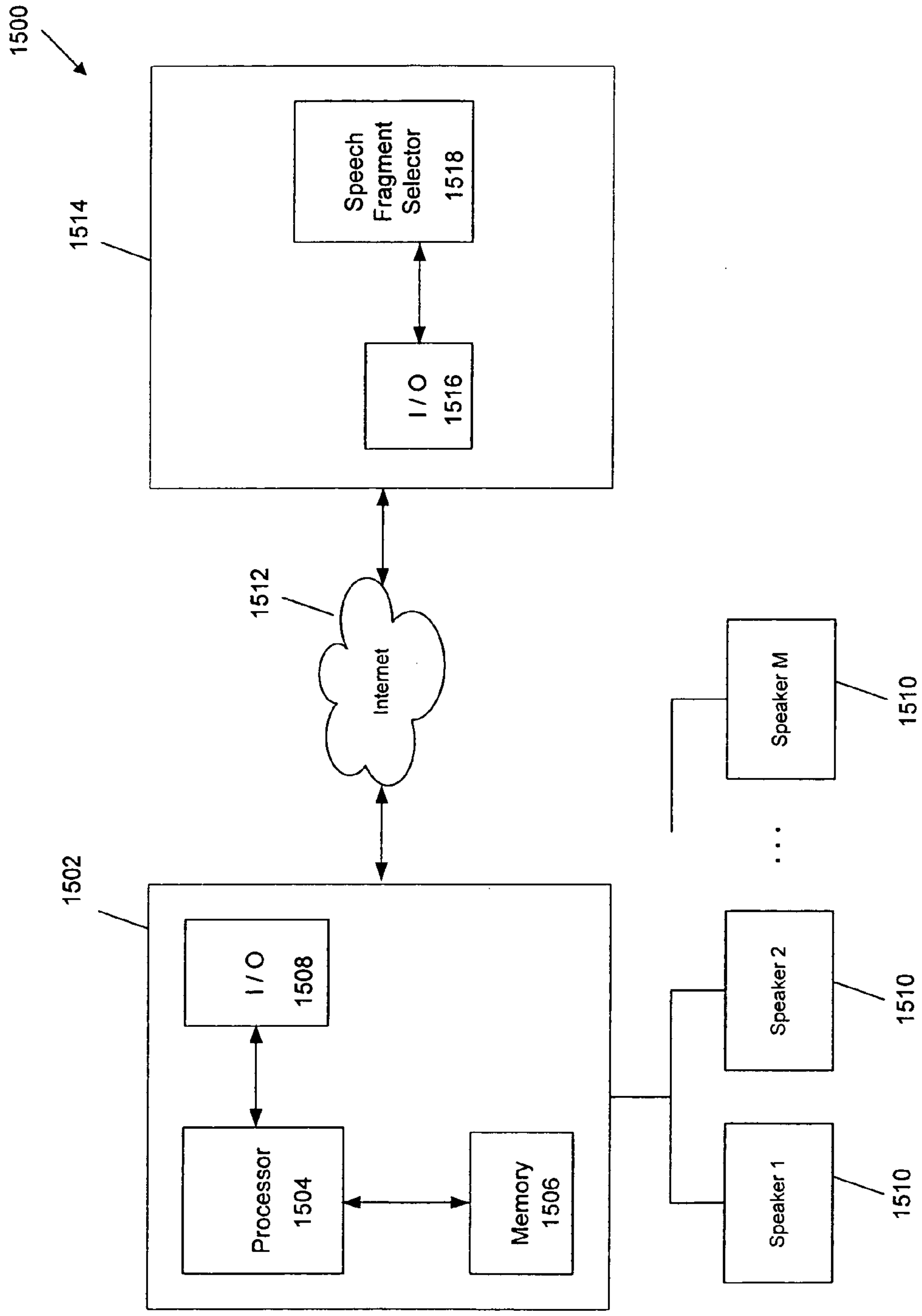
FIG. 15 is an example of a block diagram of a privacy apparatus that is configured as a distributed system.

The privacy apparatus depicted in FIG. 1 comprises one type of configuration. The privacy apparatus may have several configurations, including a self-contained and a distributed system. FIGS. 14 and 15 show examples of block diagrams of system configurations, including a self-contained system and a distributed system, respectively. Referring to FIG. 14, there is shown a system 1400 that includes a main unit 1402 and loudspeakers 1410. The main unit may include a processor 1404, memory 1406, and input/output (I/O) 1408. FIG. 14 shows I/O of Bluetooth, thumb drive, RFID, WI-FI, switch, and keypad. The I/O depicted in FIG. 14 are merely for illustrative purposes and fewer, more, or different I/O may be used.

Further, there may be 1, 2, or "N" loudspeakers. The loudspeakers may contain two loudspeaker drivers positioned 120 degrees off axis from each other so that each loudspeaker can provide 180 degrees of coverage. Each driver may receive separate signals. The number of total loudspeakers systems needed may be dependent on the listening environment in which it is placed. For example, some closed conference rooms may only need one loudspeaker system mounted outside the door in order to provide voice privacy. By contrast, a large, open conference area may need six or more loudspeakers to provide voice privacy.

Referring to FIG. 15, there is shown another system 1500 that is distributed. In a distributed system, parts of the system may be located in different places. Further, various functions may be performed remote from the talker. For example, the talker may provide the input via a telephone or via the internet. In this manner, the selection of the speech fragments may be performed remote to the talker, such as at a server (e.g., web-based applications server). The system 1500 may comprise a main unit 1502 that includes a processor 1504, memory 1506, and input/output (I/O) 1508. The system may further include a server 1514 that communicates with the main unit via the Internet 1512 or other network. In the present distributed system, the function of determining the speech fragment database may be determined outside of the main unit 1502. The main unit 1502 may communicate with the I/O 1516 of the server 1514 (or other computer) to request a download of a database of speech fragments. The speech fragment selector unit 1518 of the server 1514 may select speech fragments from the talker's input. As discussed above, the selection of the speech fragments may be based on various criteria, such as whether the speech fragment exhibits phoneme characteristics. The server 1514 may then download the selected speech fragments or chunks to the main unit 1502 for storage in memory 1506. The main unit 1502 may then randomly select the speech fragments from the memory 1506 and generate multiple voice streams with the randomly selected speech fragments. In this manner, the processing for generating the voice streams is divided between the server 1514 and the main unit 1502. Alternatively, the server may randomly select the speech fragments using speech fragment selector unit 1518 and generate multiple voice streams. The multiple voice streams may then be packaged for delivery to the main unit 1502. For example, the multiple voice streams may be packaged into a .wav or an MP3 file with 2 channels (i.e., in stereo) with a plurality of voice streams being summed to generate the sound on one channel and other plurality of voice streams being summed to generate the sound on the second channel. The time period for the .wav or MP3 file may be long enough (e.g., 5 to 10 minutes) so that any listeners may not recognize that the privacy sound is a .wav file that is repeatedly played. Still another distributed system comprises one in which the database is networked and stored in the memory 1506 of main unit 1502.

In summary, speech privacy is provided that is based on the voice of the person speaking, which permits the privacy to occur at lower amplitude than previous maskers for the same level of privacy. This privacy disrupts key speech interpretation cues that are used by the human auditory system to interpret speech. This produces effective results with a minimum 6 dB advantage over white/pink noise privacy technology.

The talker supplies his/her voice into a dedicated microphone in the base of the privacy apparatus to store the speech in non-volatile memory during a training mode. Once loaded into the non-volatile memory, the stored speech chunks are kept until erased by the talker. The privacy apparatus is placed into a gain setting mode in which the gain of the input device (telephone handset) is adjusted. Once the gain is adjusted, the privacy apparatus is placed into an operation mode in which the stored chunks are randomly accessed to create multiple channels of multi-voice streams of output. The connection to the input device microphone is used to monitor the talker's voice level as he/she talk on the telephone. The privacy apparatus constantly matches the output volume level of the privacy sound to the talker's voice level as they speak into the input device. Indicators and audible tones provide the user with feedback during the various modes to aid in programming and operating the privacy apparatus.

It is therefore intended that the foregoing detailed description be regarded as illustrative rather than limiting, and that it be understood that it is the following claims, including all equivalents, that are intended to define the spirit and scope of this invention. Other variations may be readily substituted and combined to achieve particular design goals or accommodate particular materials or manufacturing processes.

We claim:

1. A method of disrupting speech of at least one talker emanating from a space, the method comprising:

inputting speech from the talker during a training mode;

selecting speech fragments from the input speech;

storing the speech fragments in a memory;

accessing a plurality of speech signals in the memory;

generating at least one privacy output signal comprised of the speech signals being summed with one another so tat the speech signals at least partly overlap one another; and outputting the at least one privacy output signal so that the at least one privacy output signal disrupts the speech emanating from the space, where generating at least one privacy output signal comprises generating a plurality of voice steams, each voice stream being generated by selecting at least some of the speech signals in the memory and assembling the selected speech signals into the voice stream, and where the speech signals are based on speech from the talker.

2. The method of claim 1, where the speech signals comprise phonemes.

3. The method of claim 1, where selecting speech fragments from the input speech comprises:

determining an increase in energy level of the input speech as a beginning of the speech fragment; and determining a decrease in the energy level of the input speech as an end of the speech fragment.

4. The method of claim 1, further comprising:

selecting a first set of speech fragments from the input speech based on first predetermined criteria;

selecting a second set of speech fragments from the input speech based on second predetermined criteria;

wherein generating a plurality of voice streams comprises generating at least one voice stream from the first set of speech fragments and generating at least one voice stream from the second set of speech fragments.

5. The method of claim 1, where the speech signals are based on speech from someone other than the talker.

6. The method of claim 1, where the plurality of voice streams are uncorrelated with one another.

7. The method of claim 6, where the speech signals comprises speech fragments of the talker; and where generating a plurality of voice streams comprises, for each voice stream, randomly selecting speech fragments from the memory.

8. The method of claim 1, where the plurality of voice streams are generated by assembling the selected speech signals along with gaps into the voice stream, the gaps being sections that comprise no speech signals.

9. The method of claim 8, where time lengths of the gaps are selected within a predefined range.

10. The method of claim 9, where the time lengths of the gaps are randomly selected within the predefined range.

11. A method of disrupting speech of at least one talker emanating from a space, the method comprising:

accessing a plurality of speech signals in a memory;

generating at least one privacy output signal comprised of the speech signals being summed with one another so that the speech signals at least partly overlap one another; and outputting the at least one privacy output signal so that the at least one privacy output signal disrupts the speech emanating from the space, where the speech of the at least one talker comprises speech into a telephone handset; and further comprising:

sensing loudness of the speech of the at least one talker into the telephone handset; and determining loudness of the at least one privacy output signal based on the loudness of the speech of the at least one talker into the telephone handset.

12. A method of disrupting speech of at least one talker emanating from a space, the method comprising:

accessing a plurality of speech signals in a memory;

generating at least one privacy output signal comprised of the speech signals being summed with one another so that the speech signals at least partly overlap one another; and outputting the at least one privacy output signal so that the at least one privacy output signal disrupts the speech emanating from the space, where generating at least one privacy output signal comprises generating a plurality of voice streams, each voice stream being generated by selecting at least some of the speech signals in the memory and assembling the selected speech signals into the voice stream, where speech from a plurality of talkers emanates from the space;

where the memory comprises speech fragments from each of the plurality of talkers; and where generating a plurality of voice streams comprises generating multiple voice streams for each plurality of talkers.

13. The method of claim 12, further comprising identifying at least one of the plurality of talkers; and where accessing a plurality of speech signals in a memory comprises selecting a set of speech fragments based on identifying at least one of the talkers.

14. An apparatus for disrupting speech of at least one talker emanating from a space, the apparatus comprising:

a microphone that receives a voice of a person speaking;

a processor that generates a privacy signal, the privacy signal comprised of fragments of the voice received by the microphone being summed with one another so that the fragments at least partly overlap one another; and at least one loudspeaker for emitting the privacy signal so that the privacy signal disrupts the speech of the talker emanating from the space, where the processor receives input from a telephone regarding a level of loudness of speech input to the telephone; and where the processor determines a level of output for the privacy signal based on the level of loudness.

15. The apparatus of claim 14, where the privacy signal is comprised of a plurality of voice streams based on the voice received by the microphone.

16. The apparatus of claim 15, wherein the plurality of voice streams comprise speech fragments selected from the voice received by the microphone.

17. The apparatus of claim 16, where the processor generates the speech fragments; and further comprising a memory for storing the speech fragments.

18. The apparatus of claim 17, where the processor randomly selects the speech fragments in order for the processor to create the plurality of voice streams from the speech fragments stored in the memory.

19. The apparatus of claim 18, where the speech fragments comprise fragments that exhibit characteristics of phonemes.

20. An apparatus for disrupting speech of at least one talker emanating from a space, the apparatus comprising:

a microphone that receives a voice of a person speaking;

a processor that generates a privacy signal, the privacy signal comprised of fragments of the voice received by the microphone being summed with one another so that the fragments at least partly overlap one another; and at least one loudspeaker for emitting the privacy signal so that the privacy signal disrupts the speech of the talker emanating from the space, where the privacy signal is comprised of a plurality of voice streams based on the voice received by the microphone, where the loudspeaker includes input from a first channel and a second channel; and where the processor sums a plurality of voice streams for input on the first channel of the loudspeaker and sums a different plurality of voice streams for input on the second channel of the loudspeaker.

21. The apparatus of claim 20, where the pluralities of voice streams are uncorrelated with one another.

22. The apparatus of claim 20, where the processor receives input from a telephone regarding a level of loudness of speech input to the telephone; and where the processor determines a level of output for the privacy signal based on the level of loudness.

23. The apparatus of claim 22, where the telephone comprises a mouthpiece tat covers, at least partly, a mouth region of the talker.

24. The apparatus of claim 15, where the privacy signal comprises a plurality of voice streams composed of speech fragments based on the voice received by the microphone and gaps comprising no speech signals.

25. An apparatus for disrupting speech of at least one talker emanating from a space, the apparatus comprising:

a microphone that receives a voice of a person speaking;

a processor that generates a privacy signal, the privacy signal comprised of fragments of the voice received by the microphone being summed with one another so that the fragments at least partly overlap one another; and at least one loudspeaker for emitting the privacy signal so that the privacy signal disrupts the speech of the talker emanating from the space, where the privacy signal is comprised of a plurality of voice streams based on the voice received by the microphone, where speech from a plurality of talkers emanates from the space;

further comprising a memory comprising speech fragments from each of the plurality of talkers; and where the processor generates a plurality of voice streams comprising multiple voice streams for each the plurality of talkers.

26. The apparatus of claim 25, where the processor identifies at least one of the plurality of talkers; and where the processor selects a set of speech fragments based on identifying at least one of the talkers.

27. The method of claim 1, where the speech of the at least one talker comprises speech as the at least one talker is talking into a telephone handset; and further comprising:

sensing loudness of the speech of the at least one talker as the at least one talker is talking into the telephone handset; and determining loudness of the at least one privacy output signal based on the loudness of the speech of the at least one talker.

28. The method of claim 27, where the telephone handset is used to sense the loudness of the speech.

29. The method of claim 1, where speech from a plurality of talkers emanates from the space;

where the memory comprises speech fragments from each of the plurality of talkers; and where generating a plurality of voice streams comprises generating multiple voice streams for each the plurality of talkers.

* * * * *

UNITED STATES PATENT AND TRADEMARK OFFICE

CERTIFICATE OF CORRECTION

PATENT NO. : 7,376,557 B2
APPLICATION NO. : 11/326269
DATED : May 20, 2008
INVENTOR(S) : Jeffrey Specht et al.

It is certified that error appears in the above-identified patent and that said Letters Patent is hereby corrected as shown below:

In the Claims

In column 29, in claim 1, line 15, after "plurality of voice" delete "steams" and substitute --streams-- in its place.

In column 31, in claim 23, line 2, after "comprises a mouthpiece" delete "tat" and substitute --that-- in its place.

Signed and Sealed this

Third Day of February, 2009

JOHN DOLL
*Acting Director of the United States Patent and Trademark Office*

UNITED STATES PATENT AND TRADEMARK OFFICE

CERTIFICATE OF CORRECTION

PATENT NO. : 7,376,557 B2
APPLICATION NO. : 11/326269
DATED : May 20, 2008
INVENTOR(S) : Jeffrey Specht et al.

It is certified that error appears in the above-identified patent and that said Letters Patent is hereby corrected as shown below:

<u>In the Claims</u>

In column 29, in claim 1, line 45, after "plurality of voice" delete "steams" and substitute --streams-- in its place.

In column 31, in claim 23, line 53, after "comprises a mouthpiece" delete "tat" and substitute --that-- in its place.

This certificate supersedes the Certificate of Correction issued February 3, 2009.

Signed and Sealed this

Twenty-fourth Day of February, 2009

JOHN DOLL
*Acting Director of the United States Patent and Trademark Office*